United States Patent
Takahashi

(10) Patent No.: US 11,054,631 B2
(45) Date of Patent: Jul. 6, 2021

(54) ILLUMINATION OPTICAL SYSTEM, ENDOSCOPE OPTICAL SYSTEM, AND ENDOSCOPE

(71) Applicant: OLYMPUS CORPORATION, Tokyo (JP)

(72) Inventor: Susumu Takahashi, Iruma (JP)

(73) Assignee: OLYMPUS CORPORATION, Tokyo (JP)

( * ) Notice: Subject to any disclaimer, the term of this patent is extended or adjusted under 35 U.S.C. 154(b) by 243 days.

(21) Appl. No.: 16/137,653

(22) Filed: Sep. 21, 2018

(65) Prior Publication Data

US 2019/0107707 A1     Apr. 11, 2019

(30) Foreign Application Priority Data

Oct. 10, 2017   (JP) .............................. JP2017-197104

(51) Int. Cl.

| G02B 23/24 | (2006.01) |
|---|---|
| A61B 1/06 | (2006.01) |
| A61B 1/07 | (2006.01) |
| A61B 1/05 | (2006.01) |
| A61B 1/00 | (2006.01) |

(52) U.S. Cl.
CPC ...... *G02B 23/2461* (2013.01); *A61B 1/00096* (2013.01); *A61B 1/06* (2013.01); *A61B 1/0623* (2013.01); *A61B 1/07* (2013.01); *G02B 23/2423* (2013.01); *A61B 1/00163* (2013.01); *A61B 1/00177* (2013.01); *A61B 1/05* (2013.01); *G02B 23/243* (2013.01)

(58) Field of Classification Search
CPC .............. G02B 23/2461; G02B 23/243; A61B 1/0623; A61B 1/07; A61B 1/00096; A61B 1/06; A61B 1/00177; A61B 1/05; A61B 1/00163
See application file for complete search history.

(56) References Cited

U.S. PATENT DOCUMENTS

2014/0347878 A1   11/2014   Honda et al.

FOREIGN PATENT DOCUMENTS

| JP | 06-138400 A | 5/1994 |
|---|---|---|
| JP | 2012235821 A | * 12/2012 |
| JP | 2012235821 A | 12/2012 |
| WO | 2014/073426 A1 | 5/2014 |

* cited by examiner

*Primary Examiner* — Michael J Carey
*Assistant Examiner* — Tadios E Molla
(74) *Attorney, Agent, or Firm* — Scully, Scott, Murphy & Presser, P.C.

(57) ABSTRACT

An illumination optical system is formed into a substantially U shape or a partial shape of the substantially U shape as a cross-sectional shape viewed from a distal end side of a longitudinal axis such that an observation optical system is arranged inside, and has a plane as an incidence surface on which light directed toward the distal end side from a proximal end side along the longitudinal axis is incident, a plane as an emission surface from which the light is emitted as illumination light toward a subject, and a reflection surface which is inclined to direct the light incident on the incidence surface toward the emission surface when viewed from the distal end side of the longitudinal axis.

18 Claims, 16 Drawing Sheets

ILLUMINATION OPTICAL SYSTEM, ENDOSCOPE OPTICAL SYSTEM, AND ENDOSCOPE

CROSS REFERENCE TO RELATED APPLICATION

This application claims benefit of Japanese Application No. 2017-197104 filed in Japan on Oct. 10, 2017, the contents of which are incorporated by this reference.

BACKGROUND OF THE INVENTION

1. Field of the Invention

The present invention relates to an illumination optical system, an endoscope optical system, and an endoscope, and particularly to an illumination optical system and an endoscope optical system used for an endoscope configured to observe a sideward direction or an oblique direction, and the endoscope.

2. Description of Related Art

Conventionally, an endoscope has been widely used in an industrial field and a medical field. An endoscope configured to observe a sideward direction or an oblique direction has been known.

In the endoscope configured to observe a sideward direction or an oblique direction, when a distal end portion of a light guide for illumination is bent and formed to emit illumination light in s sideward direction or an oblique direction of a distal end portion of an insertion section, a rigid portion becomes long. In the endoscope configured to observe the sideward direction or the oblique direction, an observation window and an illumination window are arranged away from each other along a longitudinal axis of the insertion section. Accordingly, light distribution unevenness may occur in an endoscope image.

Japanese Patent Application Laid-Open Publication No. 2012-235821 proposes a side illumination optical system for endoscope including a flat reflection surface configured to reflect illumination light emitted from a distal end surface of a light guide sideward without bending the light guide and a light transmission optical system configured to guide the illumination light from the reflection surface in a sideward direction of a distal end portion. The proposed light transmission optical system has a substantially U shape in cross section perpendicular to a longitudinal axis of a distal end portion of an insertion section, and an outer side surface of the light transmission optical system has a cylindrical shape centered on an axis along the longitudinal axis of the distal end portion. According to the light transmission optical system, an observation window and an illumination window are not arranged away from each other along the longitudinal axis of the insertion section. Accordingly, no light distribution unevenness occurs in an endoscope image.

SUMMARY OF THE INVENTION

An illumination optical system according to an aspect of the present invention includes an illumination window provided in a distal end portion of an insertion section configured to be inserted into a subject, the illumination window being configured to emit illumination light in a sideward direction or an oblique direction of the distal end portion, and an optical member formed into a substantially U shape or a partial shape of the substantially U shape as a cross-sectional shape viewed from a distal end side of a longitudinal axis of the insertion section and having an incidence surface on which light directed toward the distal end side from a proximal end side along the longitudinal axis is incident, an emission surface from which the light is emitted as the illumination light toward the subject, and a reflection surface which is inclined to direct the light incident on the incidence surface toward the emission surface when viewed from the distal end side of the longitudinal axis.

An endoscope optical system according to another aspect of the present invention is an endoscope optical system provided in a distal end portion of an insertion section configured to be inserted into a subject, the endoscope optical system being configured to illuminate and observe a sideward direction or an oblique direction of the distal end portion, the endoscope optical system including an observation optical system provided in the distal end portion of the insertion section and configured to observe light captured from an observation window configured to capture light in the sideward direction or the oblique direction of the distal end portion, and an illumination optical system arranged in the distal end portion and including an optical member formed into a substantially U shape or a partial shape of the substantially U shape as a cross-sectional shape viewed from a distal end side of a longitudinal axis of the insertion section such that the observation optical system is arranged inside and having an incidence surface on which light directed toward the distal end side from a proximal end side along the longitudinal axis is incident, an emission surface from which the light is emitted as illumination light toward the subject, and a reflection surface which is inclined to direct the light incident on the incidence surface toward the emission surface when viewed from the distal end side of the longitudinal axis.

An endoscope according to still another aspect of the present invention includes an insertion section configured to be inserted into a subject, an observation window provided in a distal end portion of the insertion section and configured to capture light in a sideward direction or an oblique direction of the distal end portion, an illumination window provided in the distal end portion of the insertion section and configured to emit illumination light in the sideward direction or the oblique direction of the distal end portion, an observation optical system provided in the distal end portion of the insertion section and configured to observe the light captured from the observation window, and an illumination optical system arranged in the distal end portion and including an optical member formed into a substantially U shape or a partial shape of the substantially U shape as a cross-sectional shape viewed from a distal end side of a longitudinal axis of the insertion section such that the observation optical system is arranged inside and having an incidence surface on which light directed toward the distal end side from a proximal end side along the longitudinal axis is incident, an emission surface from which the light is emitted as the illumination light toward the subject, and a reflection surface which is inclined to direct the light incident on the incidence surface toward the emission surface when viewed from the distal end side of the longitudinal axis.

DETAILED DESCRIPTION OF THE PREFERRED EMBODIMENT(S)

Embodiments of the present invention will be described below with reference to the Drawings.

First Embodiment (Configuration of Endoscope Apparatus)

Figure 1:
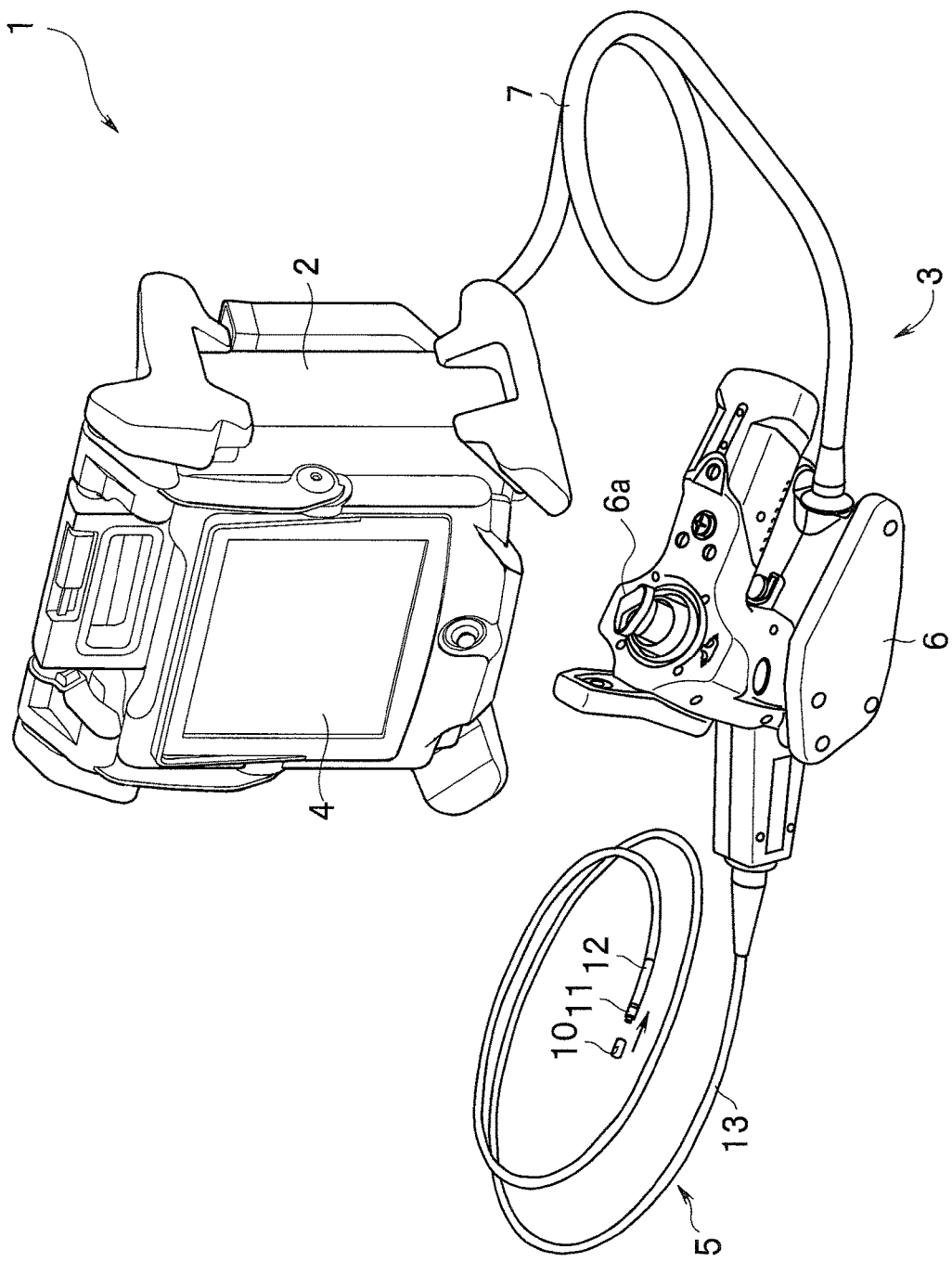
FIG. 1 is a configuration diagram illustrating a configuration of an endoscope apparatus according to a first embodiment of the present invention.

FIG. 1 is a configuration diagram illustrating a configuration of an endoscope apparatus according to the present embodiment.

As illustrated in FIG. 1, an endoscope apparatus 1 includes an apparatus body 2 having a function of a video processor or the like and an endoscope 3 connected to the apparatus body 2. The apparatus body 2 includes a display section 4 such as a liquid crystal panel (LCD (liquid crystal display)) on which an endoscope image, an operation menu, and the like are displayed. The display section 4 may be provided with a touch panel.

The endoscope 3 includes an insertion section 5 as an endoscope insertion section configured to be inserted into a subject, an operation section 6 consecutively provided at a proximal end of the insertion section 5, and a universal cord 7 extending from the operation section 6. The endoscope 3 is removably mounted on the apparatus body 2 via the universal cord 7.

The insertion section 5 includes a distal end portion 11, a bending section 12, and a longitudinal flexible portion 13 in order from its distal end side. The bending section 12 is consecutively provided at a proximal end of the distal end portion 11 and is configured to be bendable in vertical and horizontal directions, for example. The flexible portion 13 is consecutively provided at a proximal end of the bending section 12, and has flexibility.

The distal end portion 11 in the insertion section 5 contains an image pickup device 11x (FIG. 4) such as a CMOS (complementary metal oxide semiconductor) image sensor. The image pickup device 11x receives incident light incident on an observation window (not illustrated) provided in the distal end portion 11 in the insertion section 5.

An optical adapter for side view 10 can be removably mounted, as indicated by an arrow, on the distal end portion 11. The endoscope 3 becomes an endoscope for side view by mounting the optical adapter for side view 10 on the distal end portion 11.

The operation section 6 is provided with a bending joystick 6a configured to bend the bending section 12 in vertical and horizontal directions. A user can bend the bending section 12 in a desired direction by performing an operation for inclining the bending joystick 6a. The operation section 6 is provided with buttons configured to indicate an endoscope function, e.g., various types of operation buttons such as a freeze button, a bending lock button, and a recording instruction button in addition to the bending joystick 6a.

Note that in a configuration in which the display section 4 is provided with a touch panel, the user may operate the touch panel to indicate various operations of the endoscope apparatus 1.

An endoscope image picked up by the image pickup device 11×(FIG. 4) in the image pickup unit provided in the distal end portion 11 is displayed on the display section 4 in the apparatus body 2. Various types of circuits such as a control section (not illustrated) configured to perform image processing and various types of control and a recording device configured to record a processed image on a memory (not illustrated) are provided in the apparatus body 2.

(Configuration of Optical Adapter)

Figure 2:
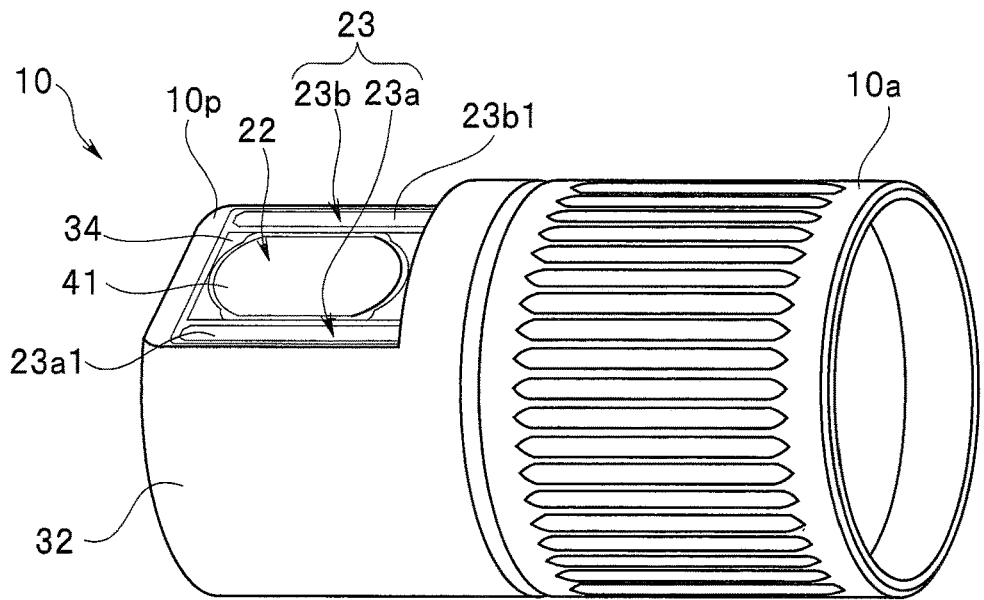
FIG. 2 is a perspective view of an optical adapter 10 according to the first embodiment of the present invention.
Figure 3:
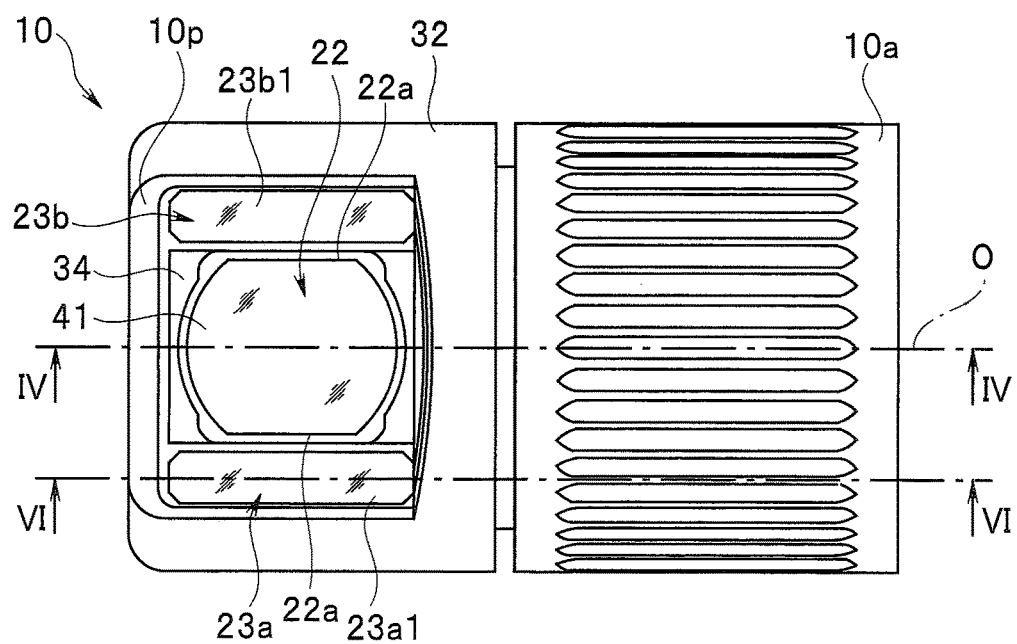
FIG. 3 is a plan view of the optical adapter 10 viewed from a subject according to the first embodiment of the present invention.
Figure 4:
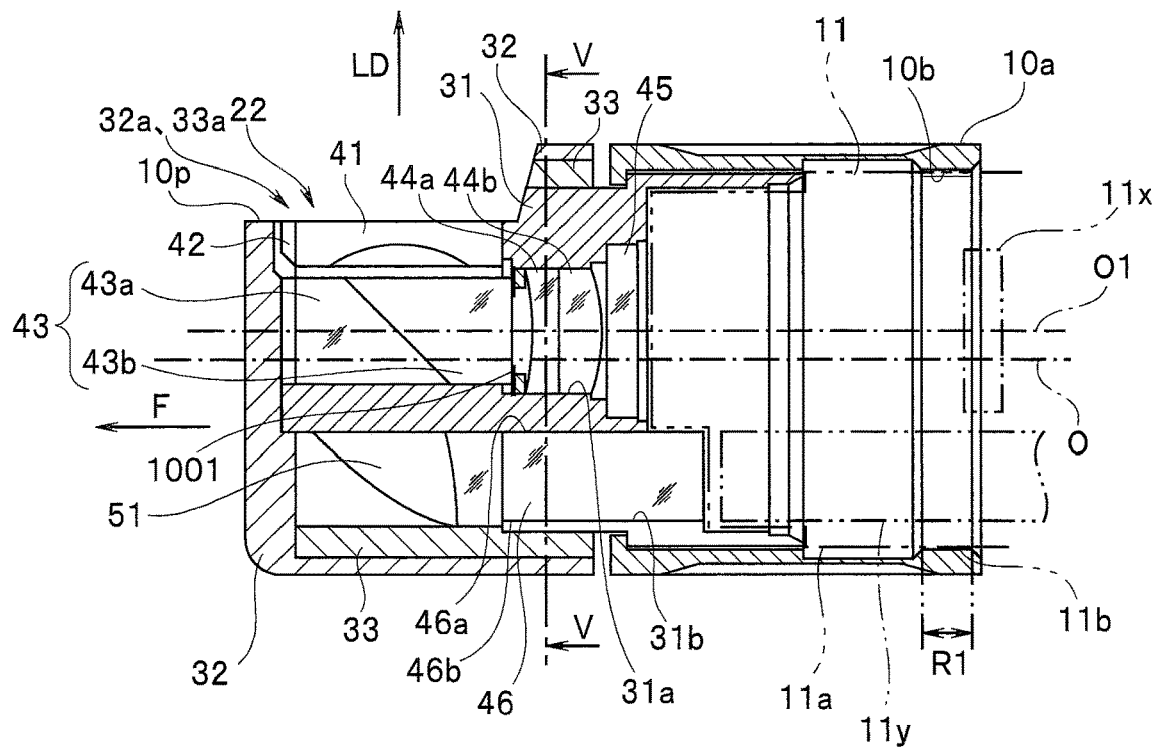
FIG. 4 is a cross-sectional view of the optical adapter 10 along a line IV-IV illustrated in FIG. 3.
Figure 5:
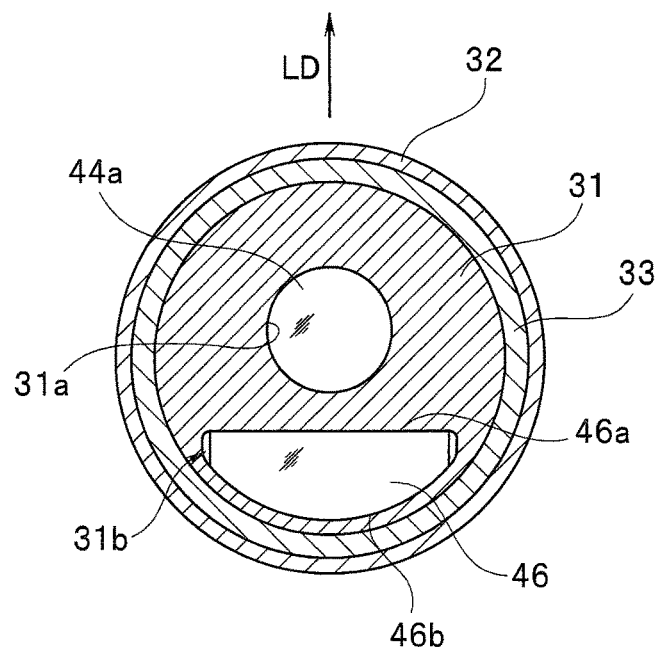
FIG. 5 is a cross-sectional view of the optical adapter 10 along a line V-V illustrated in FIG. 4.
Figure 6:
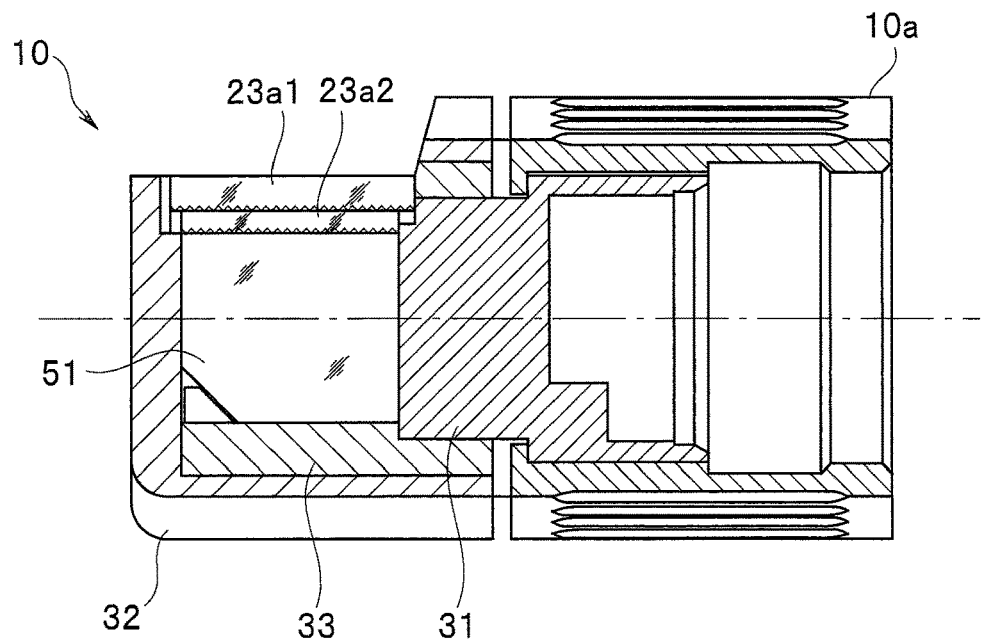
FIG. 6 is a cross-sectional view of the optical adapter 10 along a line VI-VI illustrated in FIG. 3.
Figure 7:
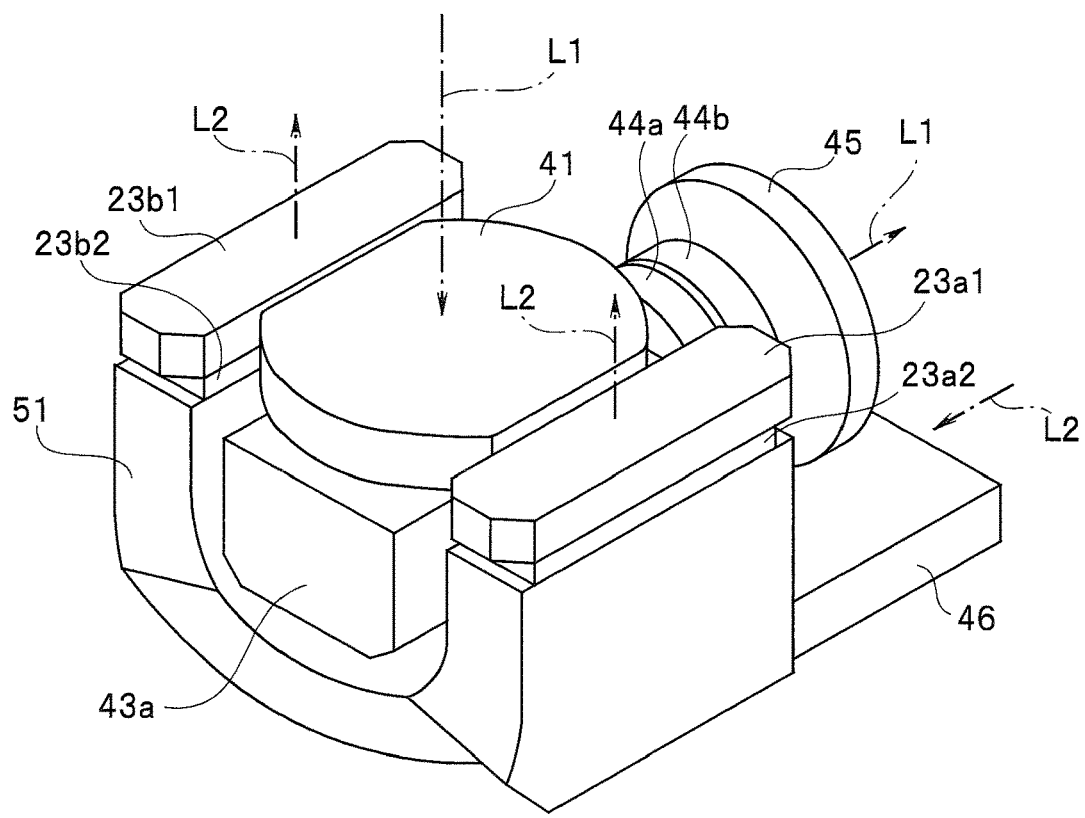
FIG. 7 is a perspective view of an image pickup optical system and an illumination optical system in the optical adapter 10 according to the first embodiment of the present invention.
Figure 8:
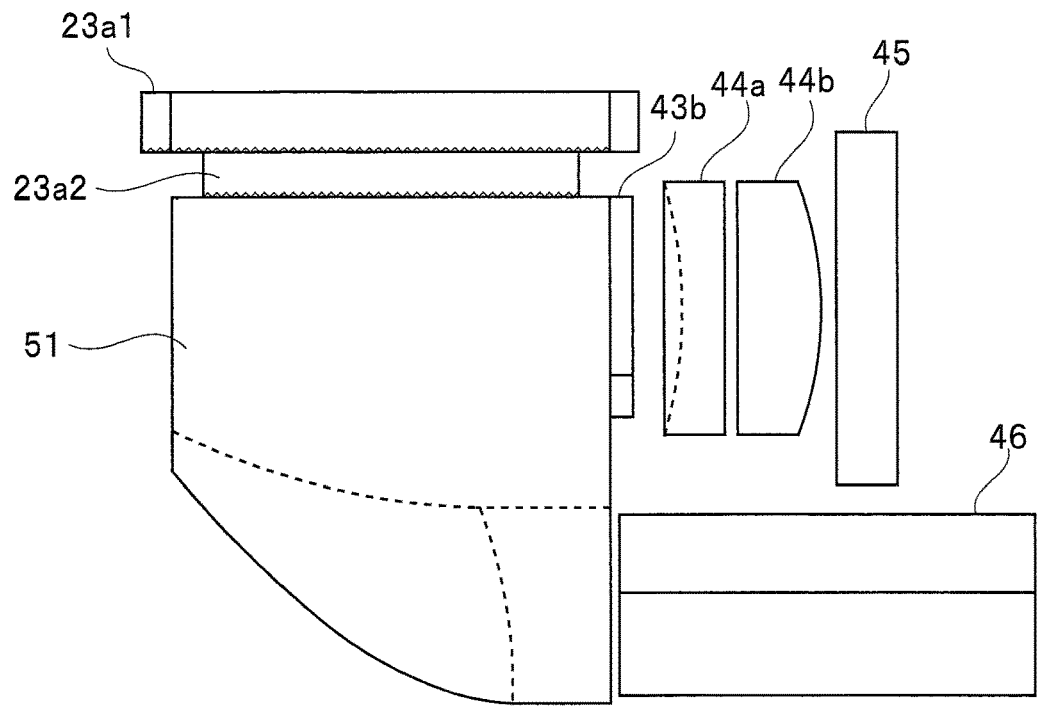
FIG. 8 is a front view of the image pickup optical system and the illumination optical system in the optical adapter 10 according to the first embodiment of the present invention.
Figure 9:
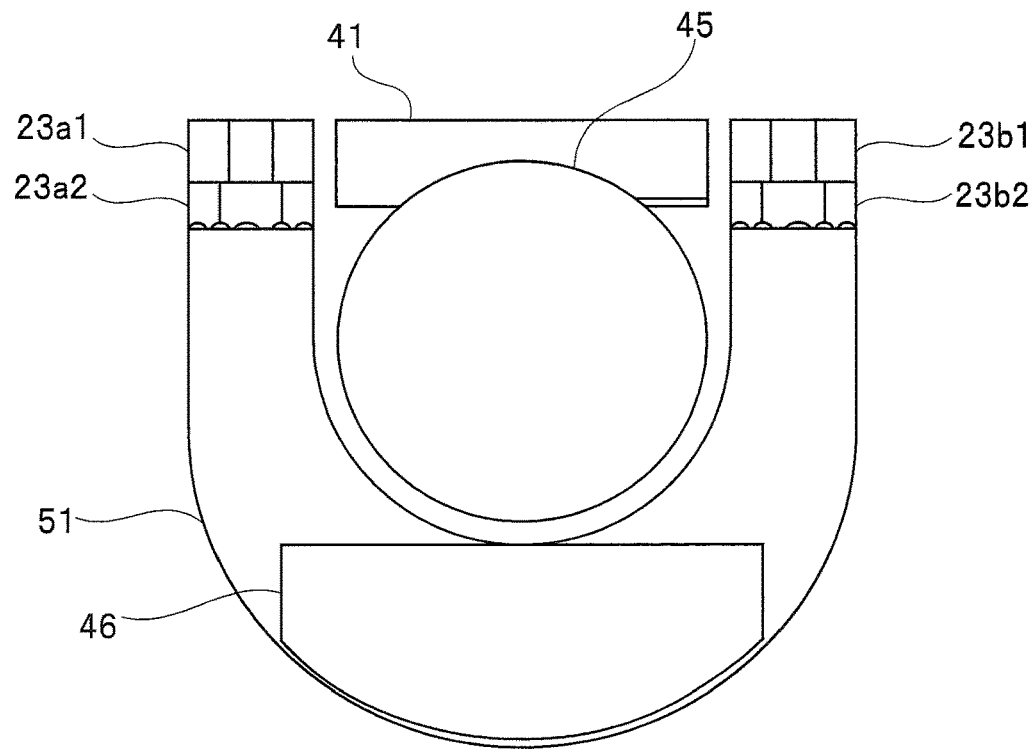
FIG. 9 is a right side view of the image pickup optical system and the illumination optical system in the optical adapter 10 according to the first embodiment of the present invention.

FIG. 2 is a perspective view of the optical adapter 10. FIG. 3 is a plan view of the optical adapter 10 viewed from the subject. FIG. 4 is a cross-sectional view of the optical adapter 10 along a line IV-IV illustrated in FIG. 3. FIG. 5 is a cross-sectional view of the optical adapter 10 along a line V-V illustrated in FIG. 4. FIG. 6 is a cross-sectional view of the optical adapter 10 along a line VI-VI illustrated in FIG. 3. FIG. 7 is a perspective view of an image pickup optical system and an illumination optical system in the optical adapter 10. FIG. 8 is a front view of the image pickup optical system and the illumination optical system in the optical adapter 10. FIG. 9 is a right side view of the image pickup optical system and the illumination optical system in the optical adapter 10.

The distal end portion 11 in the insertion section 5 includes a rigid distal end member 11a having a cylindrical shape, as indicated by a two-dot and dash line illustrated in FIG. 4, and a male screw portion 11b is formed in a partial region R1 of an outer peripheral surface of the rigid distal end member 11a.

The optical adapter for side view 10 has a columnar shape, and includes a cylindrical-shaped stop ring 10a on its proximal end side. The stop ring 10a is rotatable around a central axis of the insertion section 5 (a central axis of the distal end portion 11) O (hereinafter referred to as an axis O), and a female screw portion 10b, which can be screwed into the male screw portion 11b, is formed on an inner peripheral surface of a proximal end portion of the stop ring 10a. The axis O matches a central axis of the column-shaped optical adapter 10 when the optical adapter 10 is mounted on the distal end portion 11.

The optical adapter 10 can be mounted on and fixed to the distal end portion 11 by internally inserting the rigid distal end member 11a into the stop ring 10a and rotating the stop ring 10a in a predetermined direction to screw the male screw portion 11b and the female screw portion 10b into each other. When the stop ring 10a is rotated in the predetermined direction, an inward flange portion 10c provided in a distal end portion of the stop ring 10a presses a stepped portion 21a in an adapter body 21 in the optical adapter 10. As a result, the optical adapter 10 is firmly fixed to the distal end portion 11.

When the stop ring 10a is rotated in a direction opposite to the predetermined direction, the optical adapter 10 can be removed from the distal end portion 11.

As illustrated in FIGS. 2 and 3, an observation window for side view 22 and two illumination windows 23a and 23b provided such that the observation window 22 is sandwiched therebetween are disposed on a side surface on a distal end side of the optical adapter 10.

As illustrated in FIG. 3, the observation window 22 has a partially circular shape including two straight portions 22a by being cut on both sides along the axis O when viewed face-to-face. The two illumination windows 23a and 23b are respectively arranged adjacent to the two straight portions 22a in the observation window 22. The observation window 22 captures light from a side portion of the distal end portion 11 in the insertion section 5.

Each of the illumination windows 23a and 23b has an elongated shape extending parallel to the axis O when viewed face-to-face and has a substantially square shape obtained by chamfering four corners of a rectangle.

As illustrated in FIG. 4, a cover member 32 is fixed to an adapter body 31 in the optical adapter 10 to cover a distal end surface of the adapter body 31. The cover member 32 has a cylindrical shape which is closed on its distal end side. The column-shaped adapter body 31 is arranged to be fitted in the cylindrical member 33. The cylindrical member 33 is fixed to the adapter body 31 by fixing means such as a screw (not illustrated). The cylindrical member 33 is arranged to be fitted in the cylindrical-shaped cover member 32. The cover member 32 is fixed to the cylindrical member 33 by fixing means such as a screw (not illustrated).

The cover member 32 and the cylindrical member 33 respectively have opening portions 32a and 33a formed by being cut out along the axis O to pass through a position spaced a predetermined distance apart in an outer diameter direction from the axis O. The observation window 22 and the two illumination windows 23a and 23b are arranged in the two opening portions 32a and 33a respectively formed in the cover member 32 and the cylindrical member 33.

In the observation window 22, a plano-concave lens 41 is positioned by a positioning section 42, and is fixed to the adapter body 31, the cover member 32, and the cylindrical member 33 with an adhesive. A front surface and a rear surface of the plano-concave lens 41 are respectively a flat surface and a concave surface. Note that the positioning section 42 is formed by a part of the adapter body 31.

A prism section 43 including two prisms 43a and 43b is disposed on a back surface of the plano-concave lens 41.

A hole 31a having a cylindrical shape parallel to the axis O is formed in the adapter body 31. A lens section 44 including two lenses 44a and 44b arranged side by side along a central axis O1 of the hole 31a is disposed on a proximal end side of the prism section 43, and is fixed in the hole 31a of the adapter body 31 with an adhesive. A cover glass 45 is disposed on a proximal end side of the lens section 44, and is fixed in the hole 31a of the adapter body 31 with an adhesive.

A bonding surface between the two prisms 43a and 43b constitutes a reflection surface configured to reflect light from the plano-concave lens 41 toward the lens section 44. The reflection surface can be composed of a metal film or a multilayer film. Accordingly, the prism section 43 is fixed to the adapter body 31 with an adhesive such that the light from the plano-concave lens 41 is emitted toward the lens section 44 by changing a traveling direction of the light by 90°. The plano-concave lens 41, the prism section 43, the lens section 44, and the cover glass 45, and a lens group (not illustrated)

in the distal end portion 11 constitute an observation optical system of the endoscope 3. Respective optical axes of the prism section 43 and the lens section 44 do not match the axis O.

As described above, the plano-concave lens 41, the prism section 43, the lens section 44, and the cover glass 45 in the optical adapter 10 constitute an observation optical system configured to emit the light captured from the observation window 22 toward the proximal end side from the distal end side of the optical adapter 10 along a longitudinal axis of the distal end portion 11. Note that a brightness aperture 1001 is arranged on the proximal end side of the prism section 43.

As illustrated in FIGS. 6 to 9, in the illumination window 23a, two optical members 23a1 and 23a2 stacked in a direction perpendicular to the axis O are positioned by the positioning section 42, and are fixed to the adapter body 31, the cover member 32, and the cylindrical member 33 with an adhesive.

In the illumination window 23b, two optical members 23b1 and 23b2 stacked in the direction perpendicular to the axis O are also positioned by the positioning section 42, and are fixed to the adapter body 31, the cover member 32, and the cylindrical member 33 with an adhesive, like in the illumination window 23a. The illumination windows 23a and 23b emit illumination light toward the side portion of the distal end portion 11.

Each of the optical members 23a1 and 23b1 is an elongated and plate-shaped cover glass, and has its lower surface processed into a frosted window shape to form a diffusion surface. Each of the optical members 23a2 and 23b2 is an elongated and plate-shaped glass member having a microlens array or a micro prism array formed on its one surface close to the axis O. The optical members 23a1 and 23b1 respectively adhere to the optical members 23a2 and 23b2 with an adhesive having a different refractive index than the refractive index of the optical members 23a1 and 23b1 on the diffusion surfaces of the optical members 23a1 and 23b1 on which lights scatter. As a result, light distribution spots of illumination, which have occurred in the microlens array or the micro prism array, can be removed.

Respective front surfaces of the opening portions 32a and 33a of the cover member 32 and the cylindrical member 33, the plano-concave lens 41, and the two optical members 23a1 and 23b1 are respectively flat surfaces. Accordingly, the optical adapter 10 includes a planar portion 10p parallel to the axis O formed by the flat surfaces.

Illumination light is emitted in a direction LD perpendicular to the axis O (hereinafter referred to as an illumination direction LD) from the illumination windows 23a and 23b.

In the adapter body 31, a hole 31b for a rod lens 46 is formed along the axis O. A center of the hole 31b does not match the axis O, and the hole 31b is formed in the adapter body 31 while deviating in an outer diameter direction from the axis O. The rod lens 46 is inserted into the hole 31b, and is fixed to the adapter body 31 with an adhesive or the like. Accordingly, a cross-sectional shape of the hole 31b substantially matches a shape of an outer diameter of the rod lens 46. As illustrated in FIG. 5, a cross-sectional shape, which is perpendicular to the axis O, of the rod lens 46 is flat, a surface 46a on the side of the axis O of the rod lens 46 is a plane, and a surface 46b in the outer diameter direction of the rod lens 46 has a partially cylindrical shape protruding in the outer diameter direction.

As illustrated in FIG. 4, a light guide for illumination light 11y is inserted into the insertion section 5. A distal end surface of the light guide 11y is disposed to oppose a rear surface of an illumination window (not illustrated) of the distal end portion 11. When the optical adapter 10 is mounted on the distal end portion 11, the rod lens 46 is disposed in the optical adapter 10 such that the illumination window (not illustrated) of the distal end portion 11 is at a position opposing a proximal end surface of the rod lens 46.

A light transmission optical member 51 is disposed on a distal end side of a distal end surface of the rod lens 46, and is fixed to the adapter body 31 with an adhesive or the like.

The illumination windows 23a and 23b, the light transmission optical member 51, and the rod lens 46 constitute an illumination optical system for endoscope for the endoscope 3 including the insertion section 5 to be inserted into the subject.

As illustrated in FIG. 7, light L1 from the subject is incident on the observation window 22 from a side portion of the optical adapter 10. The light L1 is incident on the plano-concave lens 41, is reflected by the prism section 43, and is emitted toward the image pickup optical system in the distal end portion 11 via the lens section 44 and the cover glass 45.

Light L2 emitted from the distal end surface of the light guide 11y in the distal end portion 11 is incident on the proximal end surface of the rod lens 46, is incident on an incidence surface as a proximal end surface of the light transmission optical member 51 from the distal end surface of the rod lens 46, is emitted from an emission surface of the light transmission optical member 51, and is emitted toward the side portion of the optical adapter 10 from the two illumination windows 23a and 23b.

(Configuration of Light Transmission Optical Member 51)

A configuration of the light transmission optical member 51 in the illumination optical system will be described below.

Figure 10:
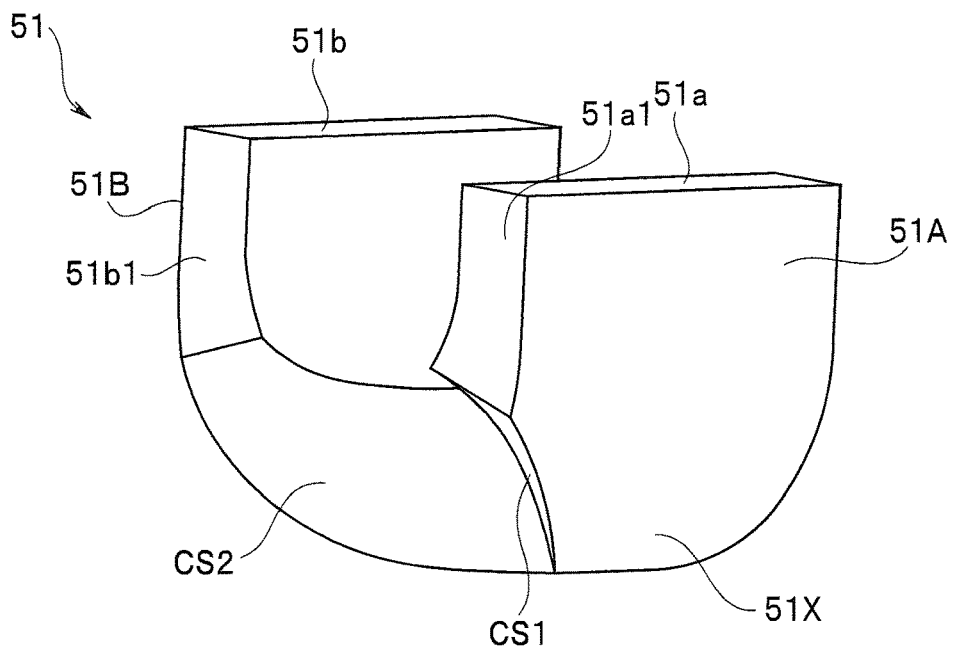
FIG. 10 is a perspective view of a light transmission optical member 51 according to the first embodiment of the present invention.
Figure 11:
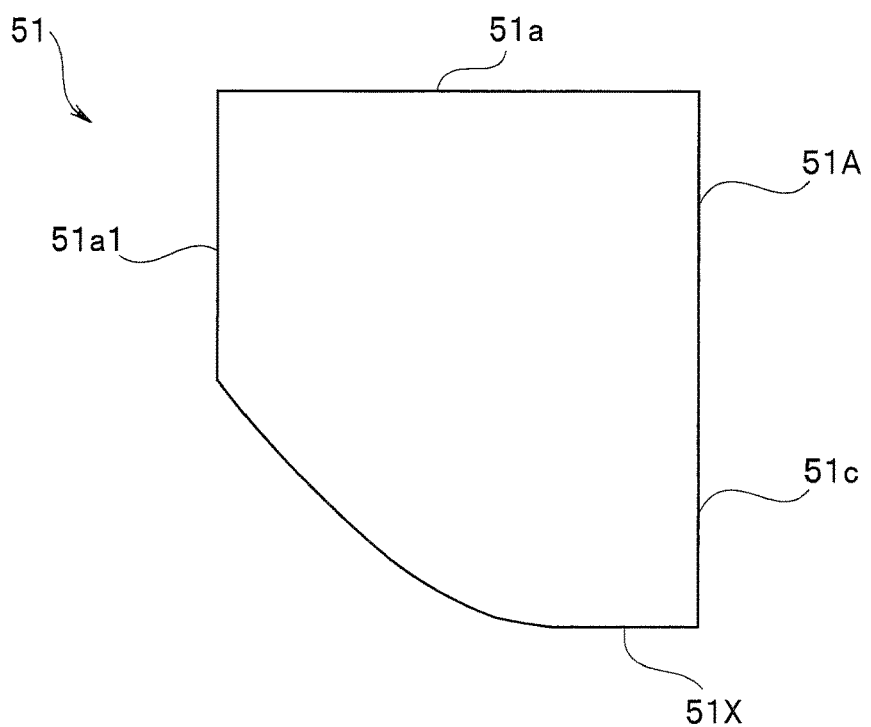
FIG. 11 is a front view of the light transmission optical member 51 according to the first embodiment of the present invention.
Figure 12:
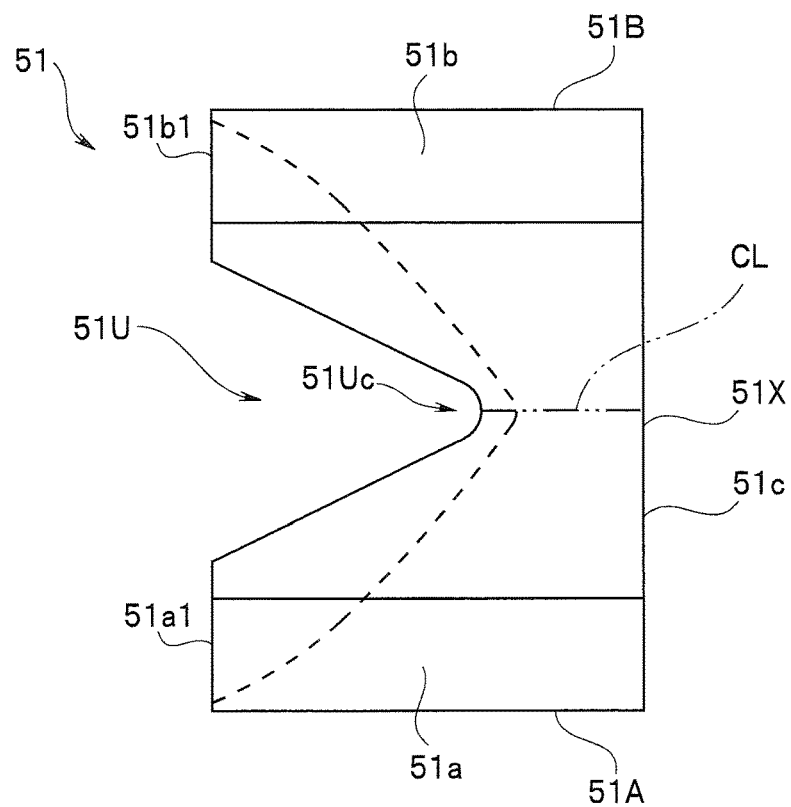
FIG. 12 is a plan view of the light transmission optical member 51 according to the first embodiment of the present invention.
Figure 13:
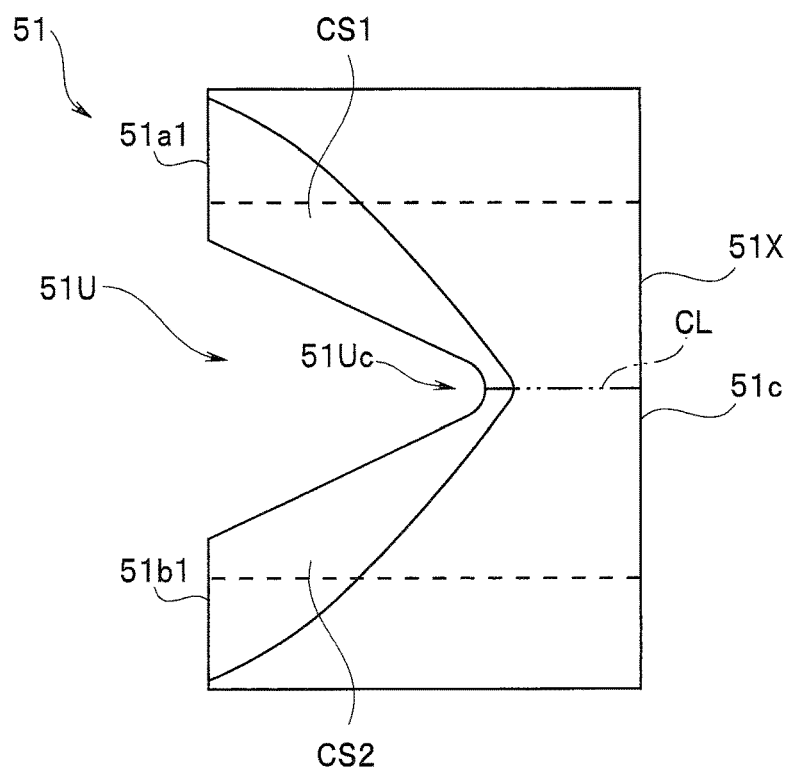
FIG. 13 is a bottom view of the light transmission optical member 51 according to the first embodiment of the present invention.
Figure 14:
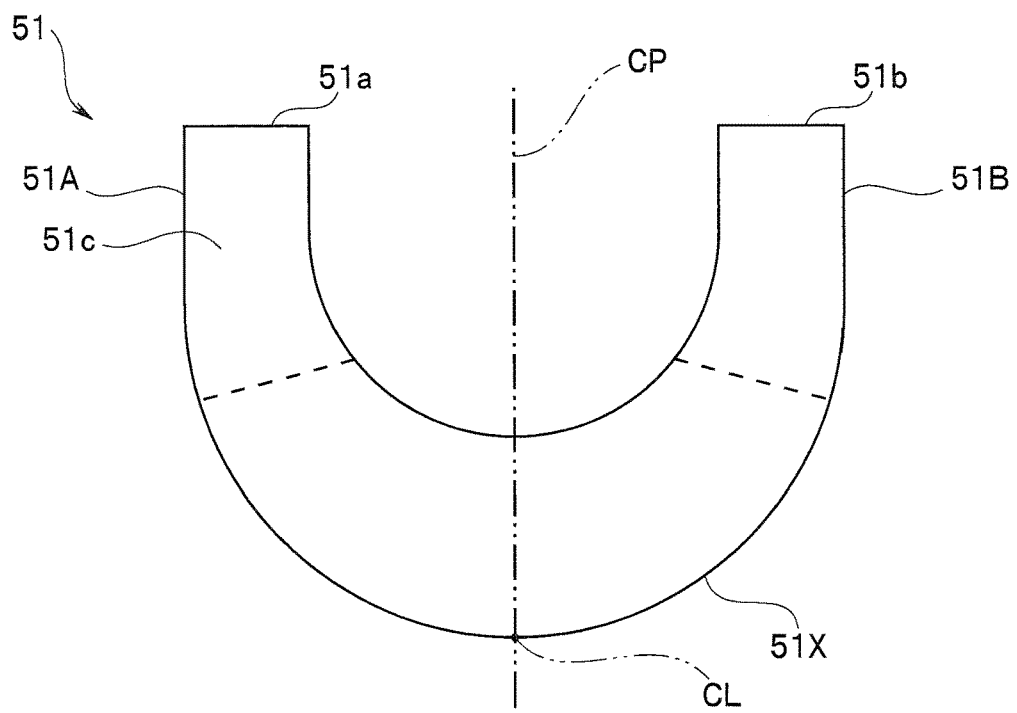
FIG. 14 is a right side view of the light transmission optical member 51 according to the first embodiment of the present invention.
Figure 15:
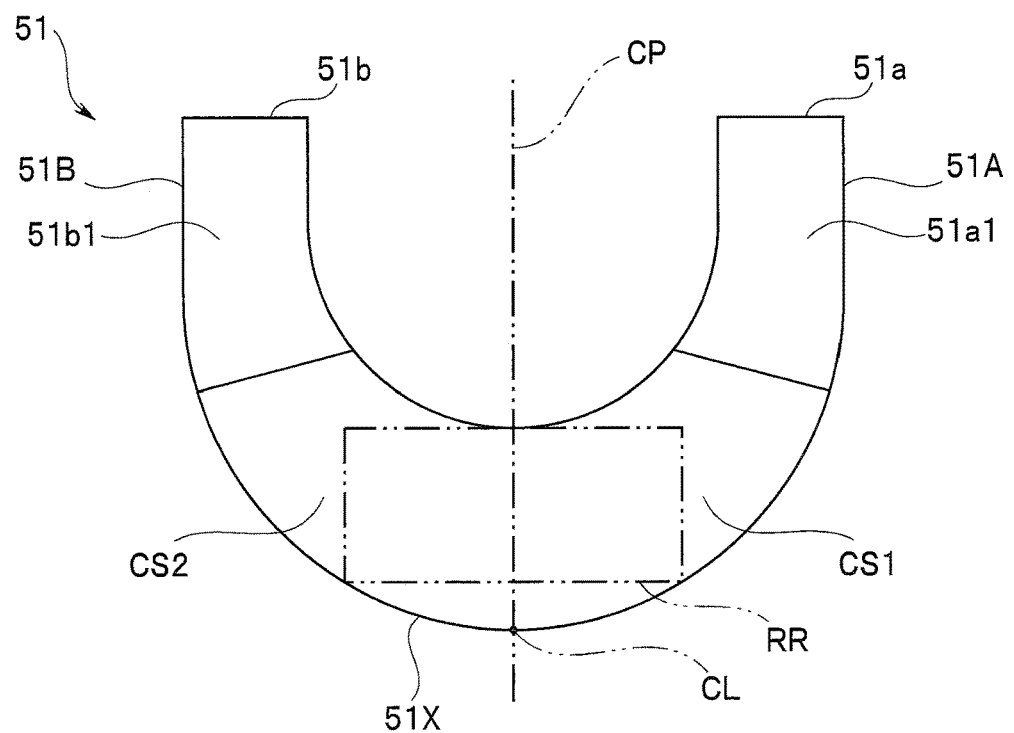
FIG. 15 is a left side view of the light transmission optical member 51 according to the first embodiment of the present invention.

FIG. 10 is a perspective view of the light transmission optical member 51. FIG. 11 is a front view of the light transmission optical member 51. FIG. 12 is a plan view of the light transmission optical member 51. FIG. 13 is a bottom view of the light transmission optical member 51. FIG. 14 is a right side view of the light transmission optical member 51. FIG. 15 is a left side view of the light transmission optical member 51.

The light transmission optical member 51 is an optical member composed of transparent glass having a substantially U shape when viewed along the axis O of the optical adapter 10.

The light transmission optical member 51 includes a partially cylindrical section 51X and two extension sections 51A and 51B extending from both ends in a circumferential direction of the partially cylindrical section 51X. The above-described prism section 43 is arranged in the light transmission optical member 51 having a substantially U shape to be surrounded by the partially cylindrical section 51X and the two extension sections 51A and 51B.

That is, the light transmission optical member 51 is formed in a substantially U shape or a partial shape of the substantially U shape as a cross-sectional shape viewed from a distal end side of the longitudinal axis such that an observation optical system is arranged inside.

A planar portion 51a is formed on an end surface of the extension section 51A, and a planar portion 51b is formed on an end surface of the extension section 51B. In the light transmission optical member 51, a direction in which the planar portions 51a and 51b in the extension sections 51A and 51B exist is also referred to as an upper direction.

A planar portion 51a1 is formed on a distal end side of the extension section 51A, and a planar portion 51b1 is formed on a distal end side of the extension section 51B. A planar portion 51c on a proximal end side of the light transmission optical member 51 has a substantially U shape. A part of the planar portion 51c, i.e., a region opposing the distal end surface of the rod lens 46 is an incidence surface of light.

As illustrated in FIGS. 12 and 13, a concave-channel section 51U is formed on a distal end side of the partially cylindrical section 51X. The concave-channel section 51U is formed in a substantially V shape when the light transmission optical member 51 is viewed from a subject to which illumination light is applied. Two reflection surfaces CS1 and CS2 as a curved surface are formed in the concave-channel section 51U in the light transmission optical member 51 toward the distal end side of the partially cylindrical section 51X from a center 51Uc of the concave-channel section 51U having the substantially V shape.

Note that, although the concave-channel section 51U has a substantially V shape including a V-shaped crest line portion rounded in manufacturing, the concave-channel section 51U desirably has a V shape including a crest line. A material for an optical member having a substantially U shape may be plastic.

The two reflection surfaces CS1 and CS2 are respectively shapes plane-symmetrical with respect to a plane CP which passes through a line CL which passes through a center of a circular arc of an outer peripheral surface of the partially cylindrical section 51X and the axis O. In other words, two reflection surfaces are plane-symmetrically provided with respect to the plane CP which passes through a central axis of the distal end portion 11.

The two reflection surfaces CS1 and CS2 are each a curved surface which has been subjected to reflection processing such as aluminum coating.

The shape of the reflection surface CS2 will be described below. Note that the reflection surface CS1 is plane-symmetrical to the reflection surface CS2, as described above, and hence description of the shape of the reflection surface CS1 is omitted.

Figure 16:
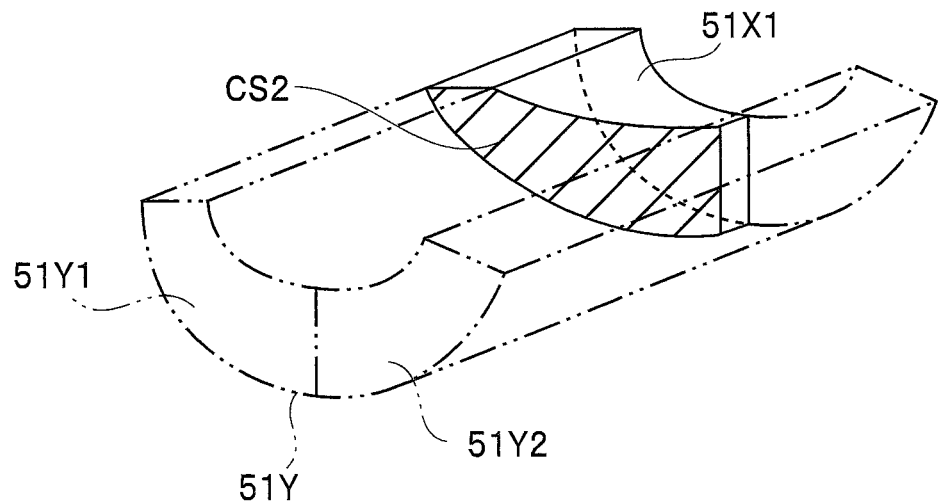
FIG. 16 is a diagram for describing a shape of a reflection surface CS2 formed on a partially cylindrical section 51X according to the first embodiment of the present invention.
Figure 17:
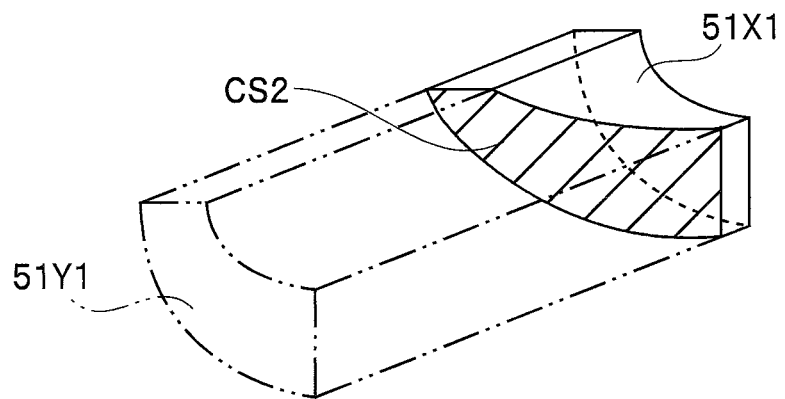
FIG. 17 is a diagram for describing a shape of a reflection surface CS2 formed on the partially cylindrical section 51X according to the first embodiment of the present invention.

FIGS. 16 and 17 are diagrams for describing the shape of the reflection surface CS2 formed on the partially cylindrical section 51X. The partially cylindrical section 51X has a shape obtained by cutting out a part of a partially cylindrical section 51Y indicated by a two-dot and dash line. The partially cylindrical section 51X is divided into two partially cylindrical sections when cut along the above-described plane CP, and one of the two partially cylindrical sections is a partially cylindrical section 51X1 indicated by a solid line.

The partially cylindrical section 51X is originally formed by cutting out a part of the partially cylindrical section 51Y indicated by a two-dot and dash line. In FIGS. 16 and 17, a part of one of two partially cylindrical sections 51Y1 and 51Y2 formed by cutting the partially cylindrical section 51Y along the above-described plane CP into two halves, i.e., the partially cylindrical section 51Y1 is the partially cylindrical section 51X1 indicated by a solid line. The reflection surface CS2 is a region indicated by an oblique line of the partially cylindrical section 51X1.

Figure 18:
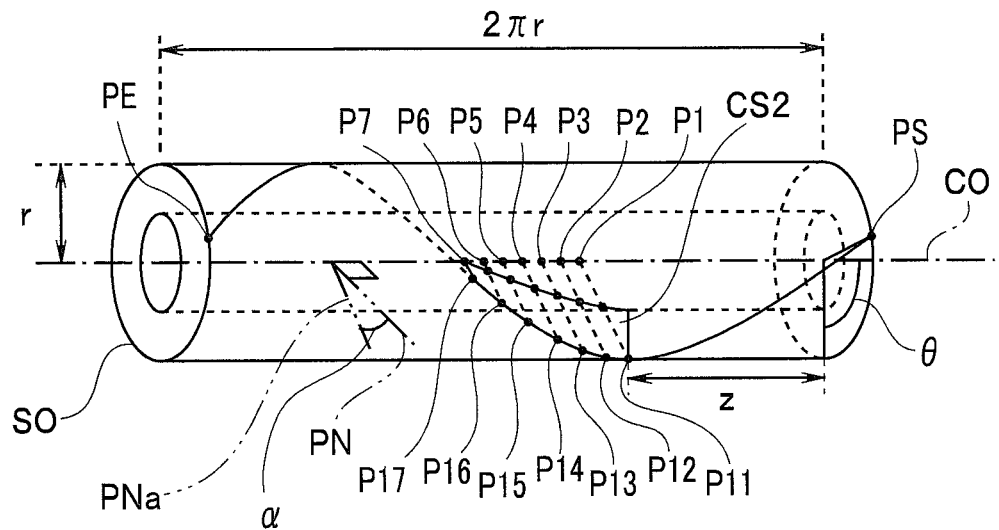
FIG. 18 is a schematic view for describing a method for forming the reflection surface CS2 according to the first embodiment of the present invention.
Figure 19:
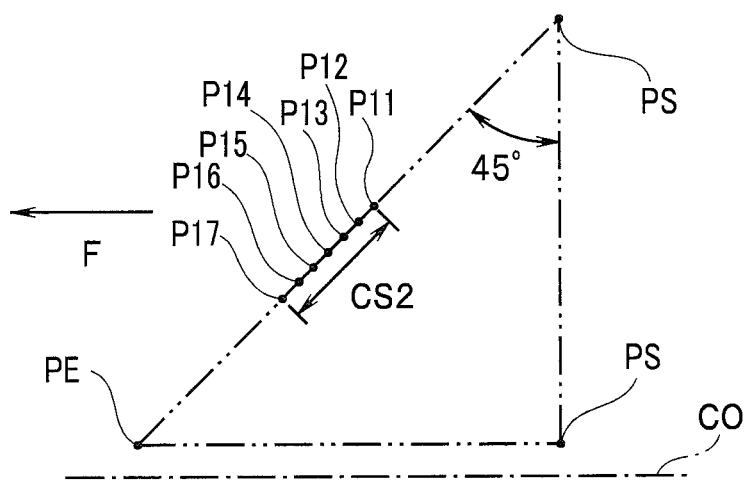
FIG. 19 is a schematic view for describing the method for forming the reflection surface CS2 according to the first embodiment of the present invention.

A method for forming a reflection surface CS2 will be described below. FIGS. 18 and 19 are schematic views for describing the method for forming the reflection surface CS2.

A cylindrical member SO having an outer diameter of r and having a length in a longitudinal axis direction of $2\pi$ is assumed. The reflection surface CS2 is a part of a cut surface formed when an outer peripheral surface of the cylindrical member SO is helically cut out at a predetermined angle (45°) to a direction of a central axis CO of the cylindrical member SO in a direction perpendicular to the central axis CO from a point PS at one end to a point PE at the other end, as illustrated in FIG. 18. The point PS and the point PE are at the same position in a circumferential direction when the cylindrical member SO is viewed in the longitudinal axis direction.

A cut surface formed by cutting out the cylindrical member SO along a line directed in an outer diameter direction while rotating once in an obliquely circumferential direction from the point PS to the point PE when the cylindrical member SO is viewed in the direction of the central axis CO advances by $2\pi$ in the longitudinal axis direction. The reflection surface CS2 is a part of a surface formed by helically cutting the cylindrical member SO along a line directed in the outer diameter direction from the central axis CO from the point PS to the point PE.

In FIG. 18, a line segment indicated by a dotted line from a point P1 to a point P11, a line segment indicated by a dotted line from a point P2 to a point P12, . . . , a line segment indicated by a dotted line from a point P7 to a point P17 on the center axis CO, for example, constitute the reflection surface CS2. That is, the reflection surface CS2 is a twisted surface formed on a distal end side of a light transmission optical member 51.

Letting z be a distance of each of the points P11 to P17 from a plane including the point PS, the reflection surface CS2 is an assembly of line segments represented by $z = r \times \theta \times A$, where r is a radius of the outer diameter of the cylindrical member SO, and $\theta$ is an angle (in radians) from the point PS around the central axis CO when the cylindrical member SO is viewed in the longitudinal axis direction, and A is a coefficient of 0.6 to 1.4.

Accordingly, the reflection surface CS2 has a curved surface shape in which the distance z along the central axis CO from an end surface as an incidence surface of the cylindrical member SO is represented by $z = r \times \theta \times A$ (where r is a radius of a circular arc, and $\theta$ is an angle from a predetermined position around the central axis CO, and A is a coefficient of 0.6 to 1.4).

FIG. 19 is a diagram obtained by unfolding the outer peripheral surface of the cylindrical member SO. When the cylindrical member SO is helically cut out around the central axis CO, cutting out the outer peripheral surface of the cylindrical member SO at a slope of 45° means that when the outer peripheral surface of the cylindrical member SO is unfolded, as illustrated in FIG. 19, a shape of the outer peripheral surface of the cylindrical member SO becomes an isosceles right triangle, one of two points with an angle of 45° and a point with a vertex angle of 90° each become a point PS, and the other point with an angle of 45° becomes a point PE.

That is, the reflection surface CS2 as the twisted surface is a surface obtained by cutting the outer peripheral surface having a substantially U shape of the cylindrical member SO at a predetermined angle (45°) to a central axis of the circular arc of the outer peripheral surface in a direction perpendicular to the central axis. Note that the twisted surface is also referred to as a "helical surface" in mathematical representation.

Note that, although a part of a surface formed by helically cutting out the outer peripheral surface of the cylindrical member SO at an angle of 45° as a predetermined angle to a direction of an axis O is set as the reflection surface CS2, the predetermined angle may not be 45°, but may be an angle within a range of 35° to 55°, for example.

Figure 20:
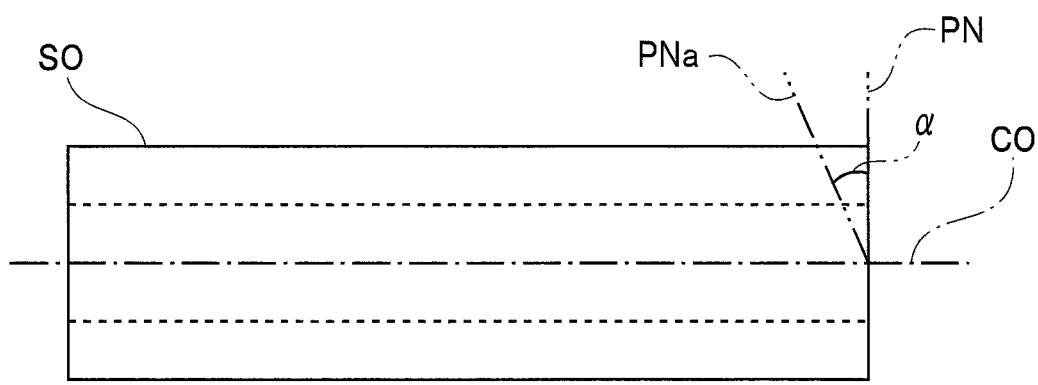
FIG. 20 is a side view of a cylindrical member SO according to the first embodiment of the present invention.

Furthermore, although in the above-described example, the reflection surface CS2 is formed by cutting the cylindrical member SO along a line segment extending in the outer diameter direction from the central axis CO, the reflection surface CS2 may be formed by cutting the cylindrical member SO along a line segment inclined by a predetermined angle α to the direction of the central axis CO in the outer diameter direction. FIG. 20 is a side view of the cylindrical member SO.

In FIGS. 18 and 20, while a line segment PN in the outer diameter direction is at a right angle to the central axis CO, a line segment PNa indicated by a two-dot and dash line is inclined by an angle α to the line segment PN in the outer diameter direction. The angle α is a tilt angle to a surface perpendicular to the central axis CO. An absolute value of tan α is not less than 0 nor more than 0.2, for example. That is, the line segment PNa is not perpendicular to the central axis CO. The reflection surface CS2 may be formed by helically cutting the cylindrical member SO along the line segment PNa.

(Function)

Then, transmission of light in the illumination optical system in the above-described optical adapter 10 will be described.

FIGS. 21 to 24 are diagrams each illustrating an optical path in the partially cylindrical section 51X1 in the light transmission optical member 51. The optical path in the partially cylindrical section 51X1 in the light transmission optical member 51 will be described below.

Figure 21:
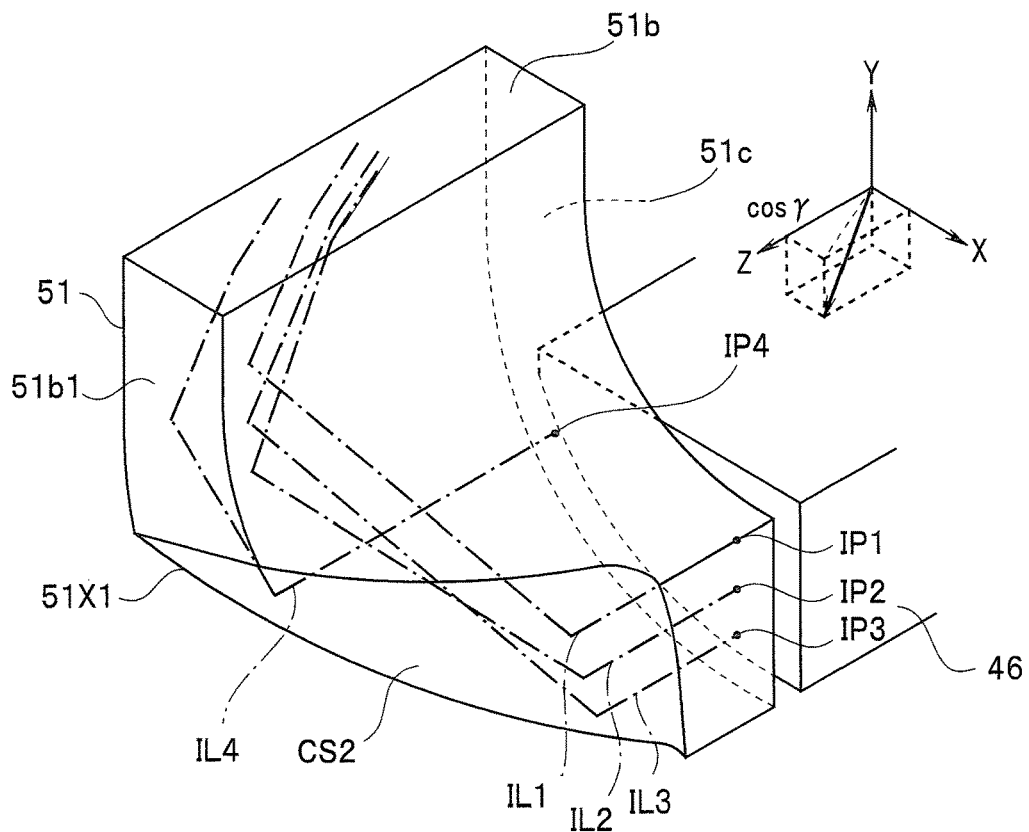
FIG. 21 is a perspective view of a partially cylindrical section 51X1 according to the first embodiment of the present invention.
Figure 22:
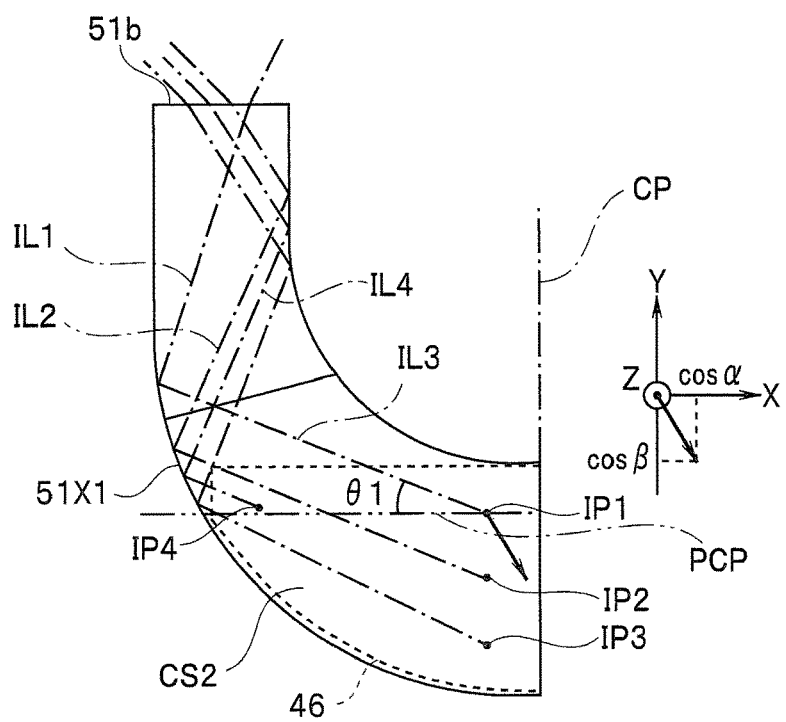
FIG. 22 is a left side view of the partially cylindrical section 51X1 according to the first embodiment of the present invention.
Figure 23:
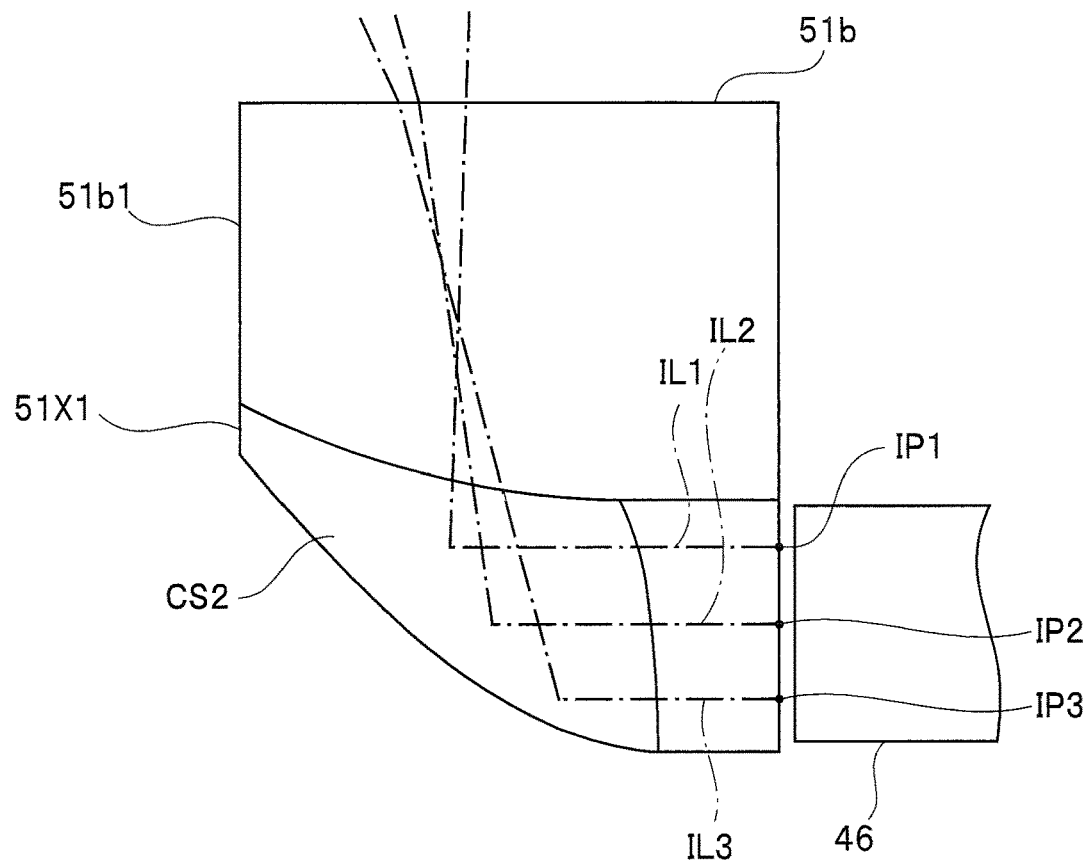
FIG. 23 is a front view of the partially cylindrical section 51X1 according to the first embodiment of the present invention.
Figure 24:
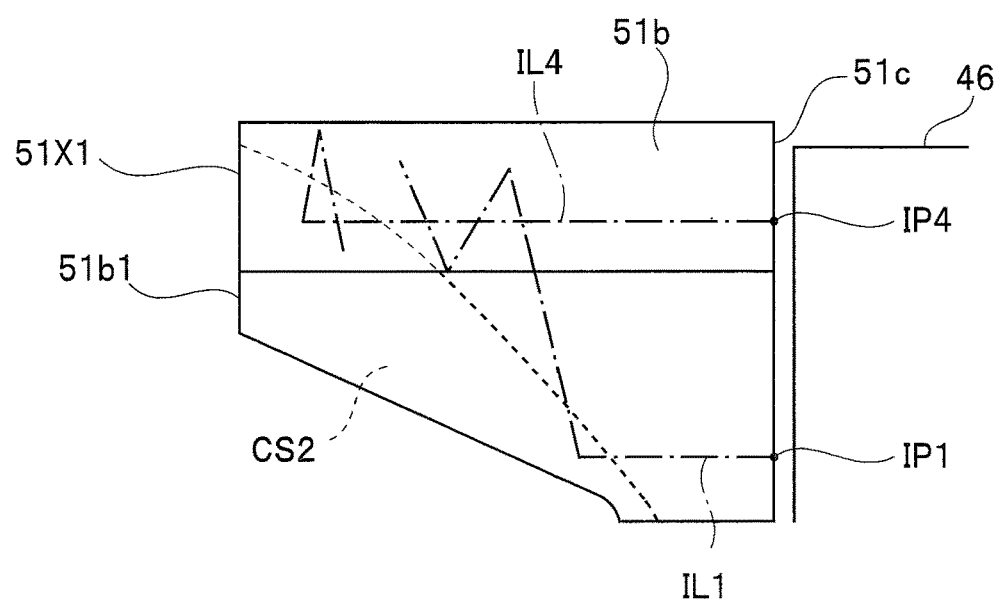
FIG. 24 is a plan view of the partially cylindrical section 51X1 according to the first embodiment of the present invention.

FIG. 21 is a perspective view of the partially cylindrical section 51X1. FIG. 22 is a left side view of the partially cylindrical section 51X1. FIG. 23 is a front view of the partially cylindrical section 51X1. FIG. 24 is a plan view of the partially cylindrical section 51X1.

Light IL1 incident on a point IP1 close to the axis O in the planar portion 51c as the incidence surface is reflected by the reflection surface CS2. The reflection surface CS2 is inclined, as described above. Accordingly, the light IL1 is not reflected in a direction perpendicular to the plane CP on the reflection surface CS2 but is reflected in a direction bent toward the planar portion 51b as an emission surface, as illustrated in FIG. 22, when the partially cylindrical section 51X1 is viewed in the longitudinal axis direction.

That is, the light transmission optical member 51 includes the planar portion 51c as the incidence surface on which light directed toward the distal end side from the proximal end side along the longitudinal axis is incident, a planar portion 51b1 as an emission surface from which light is emitted as illumination light toward the subject, and the two reflection surfaces CS1 and CS2. Each of the reflection surfaces CS1 and CS2 is inclined to direct the light incident on the incidence surface toward the emission surface when viewed from the distal end side of the longitudinal axis.

Description is more specifically made with reference to FIGS. 21 and 22. A right-handed orthogonal coordinate system using a direction in which light emitted from the rod lens 46 travels as a positive direction of a z-axis and using a normal direction of the planar portion 51b, from which light is emitted, of the light transmission optical member 51 as a positive direction of a y-axis is used.

A normal vector at a point where light incident parallel to the z-axis crosses the reflection surface CS2 is paid attention to. When a normal vector on the reflection surface CS2 is represented as a direction cosine decomposed into respective components in directions of an x-axis, the y-axis, and the z-axis, $(x,y,z)=(\cos \alpha, \cos \beta, \cos \gamma)$ (where $\cos 2\alpha + \cos 2\beta + \cos 2\gamma = 1$).

If it is indicated using the components of the normal vector that the reflection surface CS2 is inclined to direct light incident on the incidence surface toward the emission surface, when a normal in which cos γ is positive, i.e., a normal on an outer surface of the light transmission optical member 51 (the reflection surface CS2) is considered, cos β needs to be negative. On the other hand, when a normal in which cos γ is negative, i.e., a normal on an inner surface of the light transmission optical member 51 (the reflection surface CS2) is considered, cos β needs to be positive. Accordingly, for light incident parallel to the z-axis to be directed toward the emission surface, the y-axis component (cos β) and the z-axis component (cos γ) of the normal vector at the point where the light crosses the reflection surface CS2 need to differ in sign. Therefore, in other words, the reflection surfaces CS1 and CS2 can be surfaces satisfying cos β·cos γ<0. The x-axis component cos α of the normal vector on the reflection surfaces CS1 and CS2 desirably has a component, i.e., satisfies cos α #0.

In FIG. 22, a line PCP is perpendicular to the plane CP. In FIG. 22, the light IL1 is reflected in a direction bent toward the planar portion 51b only by an angle θ1 to the line PCP. As a result, an angle of incidence when the light IL1 reflected by the reflection surface CS2 is next reflected within the partially cylindrical section 51X1 becomes a critical angle or more.

A reflection surface disclosed in Japanese Patent Application Laid-Open Publication No. 2012-235821 reflects light from a planar portion 51c in a direction perpendicular to a plane CP (i.e., a direction of a line PCP). Accordingly, an angle of incidence when light reflected by the reflection surface is next reflected within a light transmission optical member is less than a critical angle. As a result, the light leaks out of the light transmission optical member.

In an optical system disclosed in Japanese Patent Application Laid-Open Publication No. 2012-235821, a part of illumination light from the reflection surface is not totally reflected when reflected by an inner surface of a cylindrical-shaped light transmission optical system but leaks out of an outer side surface of a light transmission optical system. Particularly, in the above-described proposed configuration, when a distal end portion of a light guide is spaced apart from an outer peripheral surface of the light transmission optical system, an amount of light which leaks outward without being totally reflected increases so that transmission efficiency of illumination light is low.

However, the light IL1 in the present embodiment is reflected not in a direction perpendicular to the plane CP but the direction bent toward the planar portion 51b as the emission surface on the reflection surface CS2. Accordingly, an amount of light which leaks out of the light transmission optical member decreases.

Lights IL2 and IL3 respectively incident on points IP2 and IP3 spaced apart from the point IP1 close to the axis O in the planar portion 51c as the incidence surface are also reflected by the reflection surface CS2. The lights IL2 and IL3 are also reflected in the direction bent toward the planar portion 51b with respect to the line PCP. As a result, an angle of incidence when the lights IL2 and IL3 reflected by the reflection surface CS2 are then reflected within the partially cylindrical section 51X1 becomes a critical angle or more.

Even if a size of the distal end surface of the light guide 11y is increased to increase an amount of illumination light, to form the light guide 11y into a flat shape, as illustrated in FIG. 5, light IL4 incident on a point IP4 on the side of an outer peripheral surface of the planar portion 51c close to the axis O and as the incidence surface is also reflected in the direction bent toward the planar portion 51b with respect to the line PCP on the reflection surface CS2.

Even if the size of the distal end surface of the light guide 11y, as illustrated in FIG. 5, is increased, most of the light is totally reflected within the partially cylindrical section 51X1 without leaking out of the partially cylindrical section 51X1. Accordingly, an amount of the light does not decrease.

Note that light incident on the incidence surface is also reflected by the reflection surface CS1, like by the reflection surface CS2.

As described above, when the concave-channel section 51U is provided with the above-described two reflection surfaces CS1 and CS2, an angle of incidence when lights respectively reflected by the two reflection surfaces CS1 and CS2 are incident on an outer peripheral surface of the light transmission optical member 51 can be made a critical angle or more. Accordingly, most of the light from the light guide 11y is totally reflected to travel while being reflected toward the two illumination windows 23a and 23b. Therefore, transmission efficiency of the light can be increased.

As described above, according to the above-described embodiment, there can be provided an illumination optical system, an endoscope optical system, and an endoscope in which an amount of leakage of illumination light which leaks out without being totally reflected to improve transmission efficiency of the illumination light.

Although the reflection surfaces CS1 and CS2 of the above-described light transmission optical member 51 are each a curved surface, the curved surface may be a plurality of polyhedrons. In the case, the polyhedrons are formed along the curved surfaces of the reflection surfaces CS1 and CS2. Accordingly, most of the light from the light guide 11y is totally reflected within the light transmission optical member 51, is emitted from two emission surfaces, and is directed toward illumination windows.

Note that a center position of a circular arc of an inner peripheral surface and a center position of a circular arc of an outer peripheral surface of the above-described partially cylindrical section 51X differ from each other. Accordingly, a middle portion of the partially cylindrical section 51X expands, as illustrated in FIG. 14. That is, the substantially U shape of the partially cylindrical section 51X is formed by two circular arcs, which differ in central position, of two circles.

Note that the substantially U shape of the partially cylindrical section 51X may be a shape in which the center position of the circular arc of the inner peripheral surface and the center position of the circular arc of the outer peripheral surface match each other.

Second Embodiment

Although the reflection surface of the light transmission optical section provided in the optical adapter is a curved surface in the first embodiment, a reflection surface of a light transmission optical section provided in an optical adapter is a plane in a second embodiment.

Respective configurations of an endoscope and the optical adapter according to the second embodiment are respectively substantially the same as the configurations of the endoscope and the optical adapter according to the first embodiment. Accordingly, in the second embodiment, description of the same components as the components in the first embodiment is omitted, and only different components will be described.

While the configuration of the optical adapter according to the present embodiment is substantially the same as the configuration of the optical adapter 10 according to the first embodiment, and a shape of a light transmission optical member 51XA in the optical adapter is also substantially the same as the shape of the light transmission optical member 51 illustrated in FIGS. 10 to 17, a shape of two reflection surfaces CS1A and CS2A formed in a concave-channel section differs from the shape of the two reflection surfaces CS1 and CS2 in the first embodiment. Accordingly, the shape of the two reflection surfaces CS1A and CS2A of the optical adapter according to the present embodiment will be described below.

The two reflection surfaces CS1A and CS2A also respectively have shapes plane-symmetrical with respect to a plane CP, described above. Therefore, the shape of the reflection surface CS2A is mainly described, and description of the shape of the reflection surface CS1A is omitted.

Figure 25:
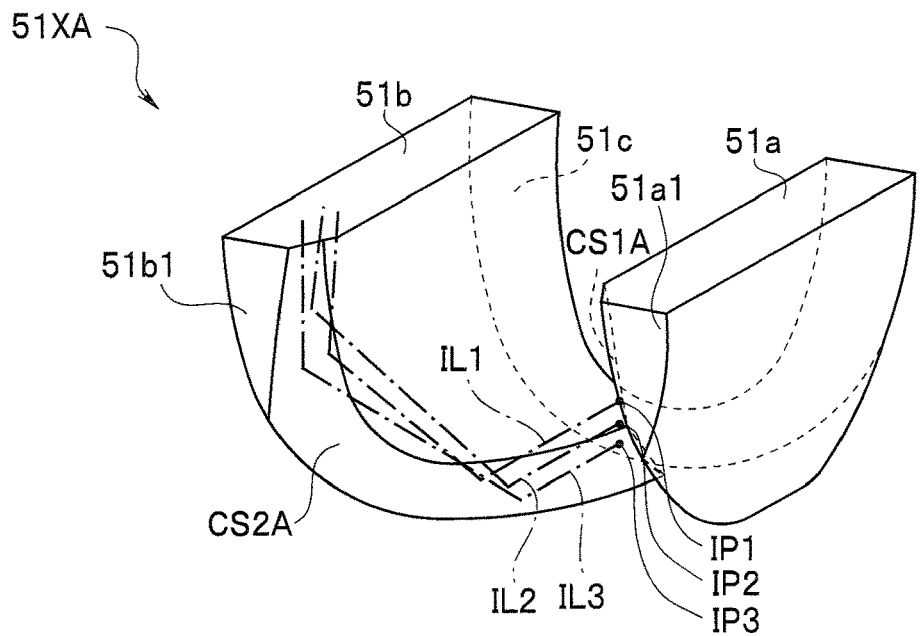
FIG. 25 is a perspective view of a light transmission optical member 51XA obliquely viewed from a distal end side according to a second embodiment of the present invention.

FIG. 25 is a perspective view of a light transmission optical member 51XA obliquely viewed from its distal end side. FIGS. 26 to 29 are diagrams for describing the respective shapes of the two reflection surfaces CS1A and CS2A.

The reflection surfaces CS1A and CS2A are respectively surfaces formed in the following manner.

Figure 26:
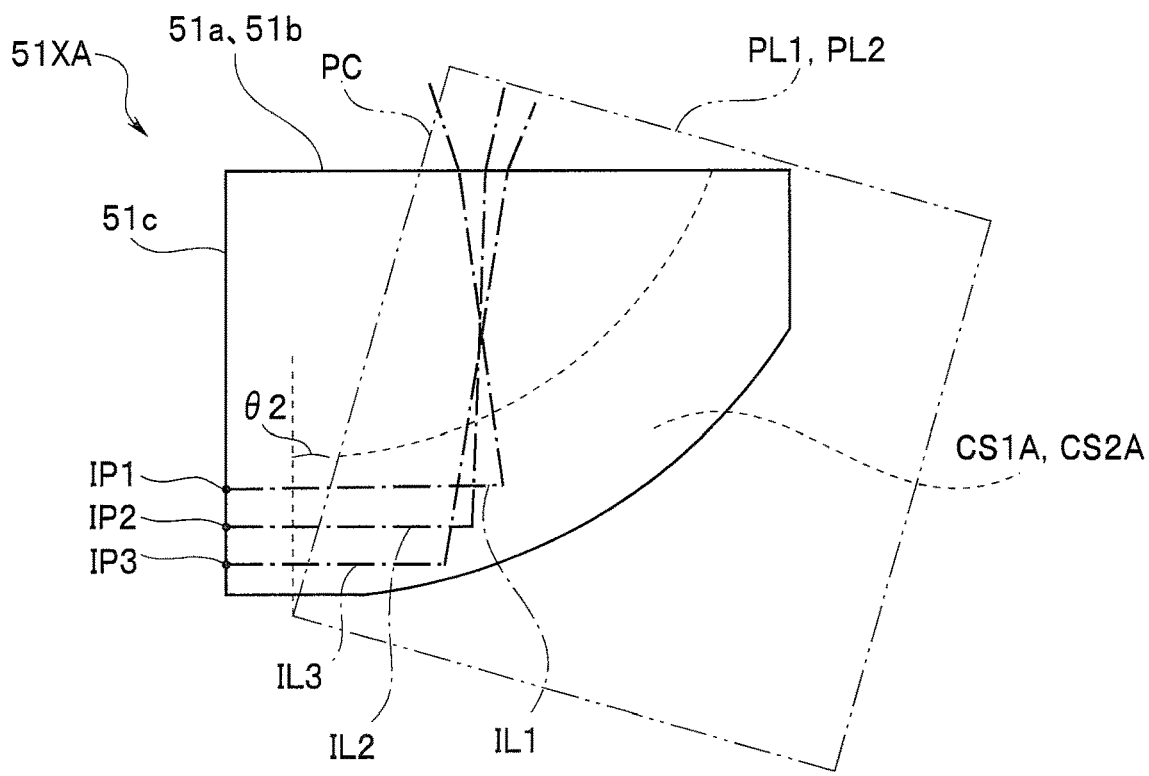
FIG. 26 is a front view of the light transmission optical member 51XA having a substantially U shape according to the second embodiment of the present invention.
Figure 27:
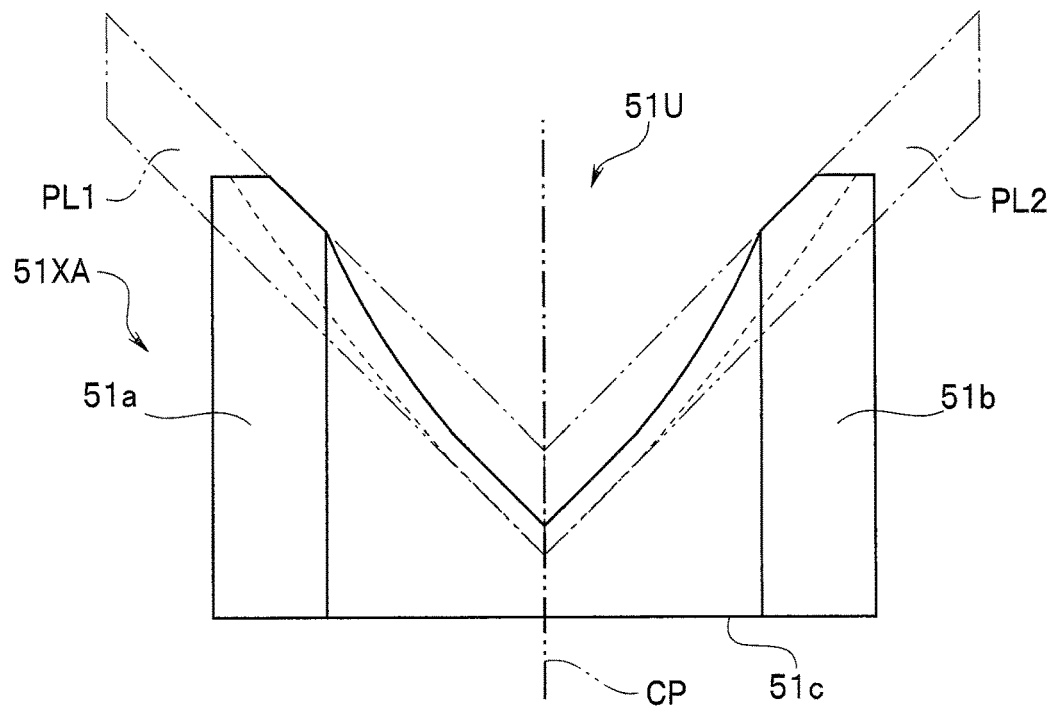
FIG. 27 is a plan view of the light transmission optical member 51XA according to the second embodiment of the present invention.
Figure 28:
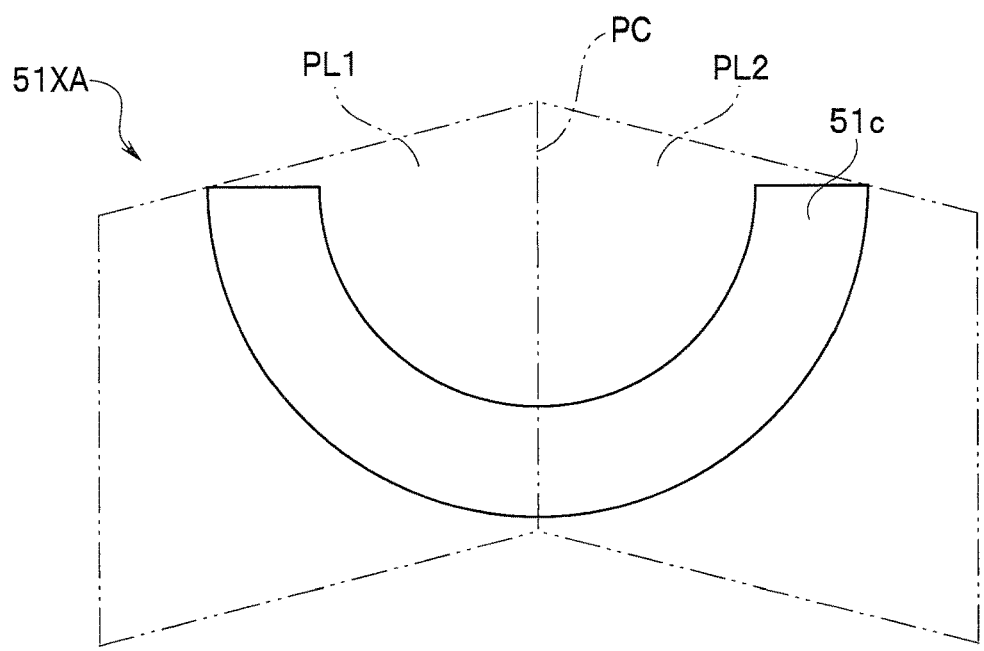
FIG. 28 is a left side view of the light transmission optical member 51XA viewed from a proximal end side according to the second embodiment of the present invention.
Figure 29:
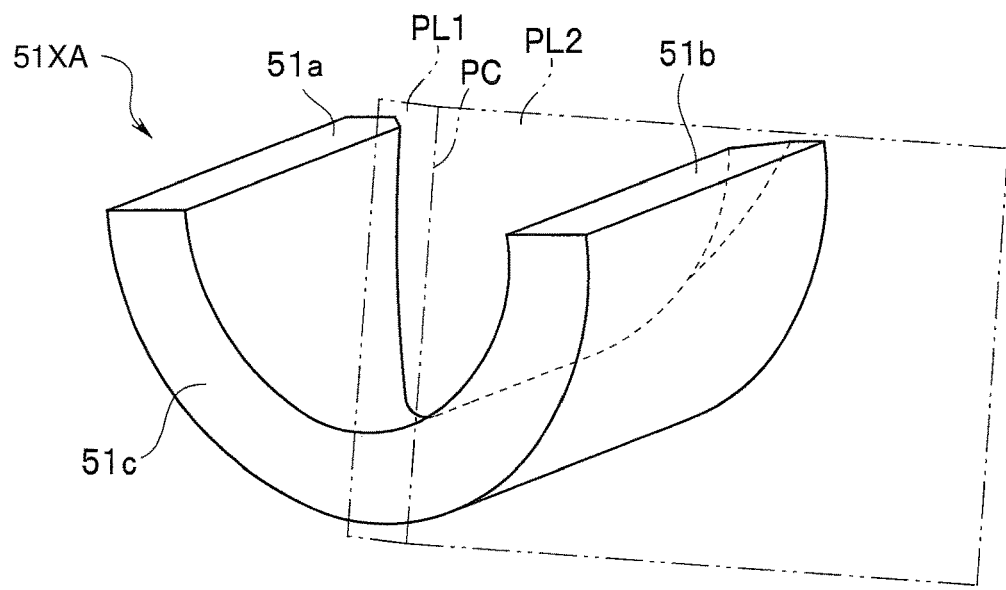
FIG. 29 is a perspective view of the light transmission optical member 51XA obliquely viewed from a proximal end side according to the second embodiment of the present invention.

FIG. 26 is a front view of the light transmission optical member 51XA having a substantially U shape. FIG. 27 is a plan view of the light transmission optical member 51XA. FIG. 28 is a left side view of the light transmission optical member 51A viewed from its proximal end side. FIG. 29 is a perspective view of the light transmission optical member 51XA obliquely viewed from the proximal end side.

In a cross section of the light transmission optical member 51XA having the substantially U shape in the present embodiment, respective center positions of circular arcs of an inner peripheral surface and an outer peripheral surface of the light transmission optical member 51XA match each other, and the circular arc of the inner peripheral surface and the circular arc of the outer peripheral surface are respectively parts of concentric circles. That is, in the present embodiment, the substantially U shape of the light transmission optical member 51XA is formed by the respective circular arcs of the two concentric circles.

Two planes PL1 and PL2 which are opened only by 90° are assumed. When an upper portion of a plane CP where a center line PC between the two planes PL1 and PL2 passes through a center of the outer peripheral surface of the light transmission optical member 51XA is inclined by an angle θ2 toward the distal end side of the light transmission optical member 51XA, two surfaces formed in the light transmission optical member 51XA by cutting along the two planes PL1 and PL2 are respectively reflection surfaces CS1A and CS2A.

That is, a portion, where the two planes PL1 and PL2 cross each other, of the center line PC is an edge line. The center line PC is inclined only by a predetermined angle θ2 (15°) downward in FIG. 26 within the plane CP. Two surfaces formed in the light transmission optical member 51XA by cutting along the two planes PL1 and PL2 are respectively the reflection surfaces CS1A and CS2A. In other words, a portion in an illumination direction LD of the edge line as the portion where the two planes PL1 and PL2 cross each other is inclined toward the distal end side.

The two reflection surfaces CS1A and CS2A are respectively formed by cutting along the two planes PL1 and PL2. That is, each of the reflection surfaces CS1A and CS2A is a plane formed on the distal end side of the light transmission optical member 51XA having the substantially U shape. The two reflection surfaces CS1A and CS2A are plane-symmetrical with respect to the plane CP which passes through a central axis of a distal end portion 11.

Light IL1 incident on a point IP1 close to an axis O in a planar portion 51c as an incidence surface is also reflected by the reflection surface CS2A thus formed, like in the first embodiment. The reflection surface CS2A is inclined, as described above. Accordingly, the light IL1 is not reflected in a direction perpendicular to the plane CP on the reflection surface CS2A but is reflected in a direction bent toward a planar portion 51b as an emission surface, as illustrated in FIGS. 25 and 26, when the light transmission optical member 51XA is viewed in a longitudinal axis direction.

Here, the reflection surfaces CS1A and CS2A are each a surface on which light incident parallel to a z-axis is directed toward the emission surface, like in the first embodiment, and the reflection surfaces CS1A and CS2A can also be referred to as a surface satisfying $\cos\beta\cdot\cos\gamma<0$.

Lights IL2 and IL3 respectively incident on points IP2 and IP3 spaced apart from the point IP1 close to the axis O in the planar portion 51c as the incidence surface are also reflected by the reflection surface CS2A, like in the first embodiment. The lights IL2 and IL3 are also reflected in the direction bent toward the planar portion 51b with respect to a direction perpendicular to the plane CP.

Accordingly, according to the above-described embodiment, there can also be provided an illumination optical system, an endoscope optical system, and an endoscope in which an amount of leakage of illumination light without being totally reflected is reduced to improve transmission efficiency of the illumination light.

Modifications will be described below.
(Modification 1)

Although light transmission optical members 51 and 51A are each one member in the above-described two embodiments, the one member may be divided into two parts along the plane CP. That is, one optical member having reflection surfaces CS1 and CS1A and one optical member having reflection surfaces CS2 and CS2A respectively constitute the light transmission optical members 51 and 51A.

If the number of light guides configured to emit illumination light to each of the two optical members is set to two, a case where two illumination lights are applied and a case where only one illumination light is applied can be switched.
(Modification 2)

Although in the above-described two embodiments, the two illumination windows are disposed such that an observation window is sandwiched therebetween, the number of illumination windows may be one. Therefore, the reflection surfaces in each of the above-described two embodiments can also be applied to a case where the number of illumination windows is one.

Figure 30:
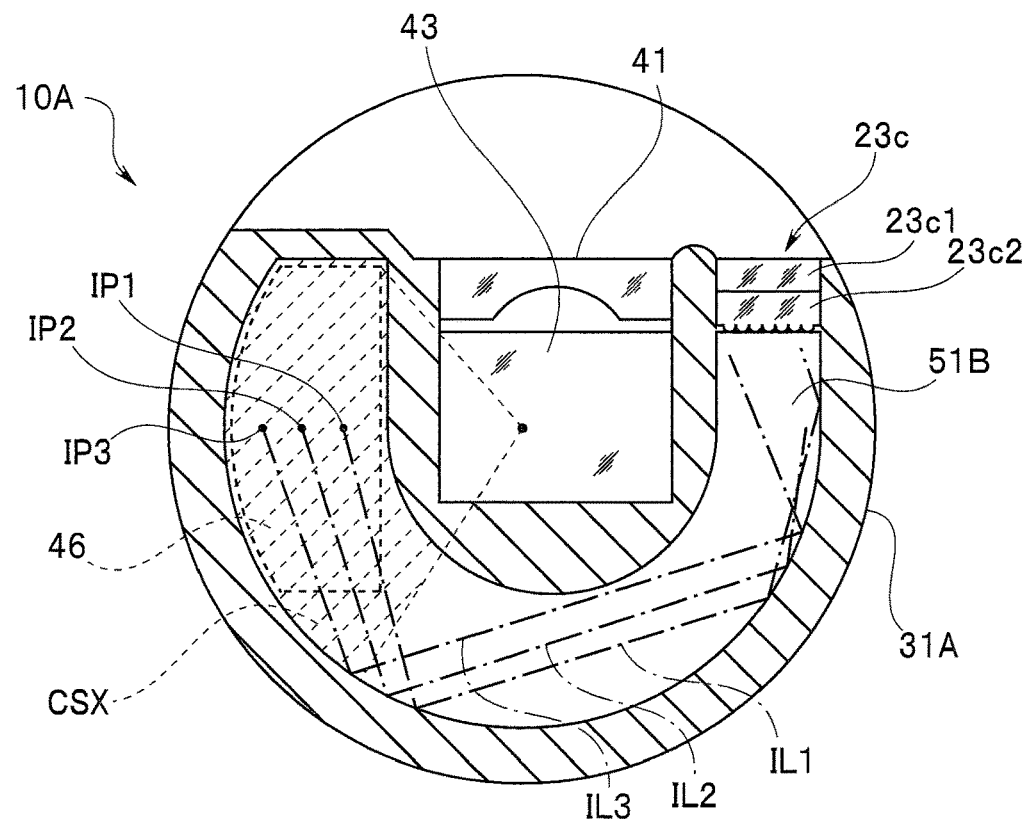
FIG. 30 is a schematic sectional view of an optical adapter including one illumination window according to a modification 2 to the two embodiments of the present invention.

FIG. 30 is a schematic sectional view of an optical adapter including one illumination window. FIG. 30 is a cross-sectional view of an optical adapter 10A viewed from its distal end side.

A light transmission optical member 51B having a substantially U shape is disposed and fixed in an adapter body 31A. A distal end surface of a rod lens 46 is arranged on a proximal end surface closer to one end of the light transmission optical member 51B having the substantially U shape. Optical members 23c1 and 23c2 constituting an illumination window 23c are provided on an end surface at the other end of the light transmission optical member 51B having the substantially U shape. Both surfaces of the optical member 23c1 are respectively planes, like in the above-described optical member 23a1, and the optical member 23c2 is an elongated and plate-shaped glass member in which a microlens array is formed on a surface on the side of the light transmission optical member 51B and a diffusion surface is formed by processing the other surface into a frosted glass shape, like the above-described optical member 23a2. Both surfaces of the optical member 23c2 are respectively planes, like in the optical member 23a2.

A reflection surface CSX (indicated by dotted hatching) as a curved surface or a plane is provided, like the reflection surfaces CS2 and CS2A respectively described in the first and second embodiments, on a distal end side of the light transmission optical member 51B.

In the light transmission optical member 51B illustrated in FIG. 30, the reflection surface CSX also reflects light from the rod lens 46 to totally reflect the light within the light transmission optical member 51B, like the above-described reflection surfaces CS2 and CS2A.

When illumination light from one illumination window is used, a subject can be observed by highlighting unevenness on a surface of the subject.
(Modification 3)

Although in the above-described embodiments and other modifications, the reflection surface of the light transmission optical member is a plane obtained by cutting out a partially cylindrical member along an inclined surface or a plane helically cut out around an axis, only a region, which matches a shape of a distal end surface of a light guide, of the light transmission optical member may be set as a reflection surface when the light transmission optical member is viewed from the distal end side.

Only a region RR having a rectangular shape may be subjected to reflection processing such that only a region matching a shape of a partial circle as illustrated in FIG. 9 is set as a reflection surface when the light transmission optical member is viewed from the distal end side if the shape of the distal end surface of the light guide is the shape of the partial circle and only the region RR matching a rectangular shape as indicated by a two-dot and dash line in FIG. 15 is set as a reflection surface when the light transmission optical member is viewed from a distal end side in a longitudinal axis direction if the shape of the distal end surface of the light guide is the rectangular shape, for example. That is, a shape of each of the reflection surfaces may be a rectangle when viewed in the longitudinal axis direction.
(Modification 4)

Although in the above-described embodiments and other modifications, the side illumination optical system including the light transmission optical member is provided in the optical adapter 10, and the optical adapter 10 is mounted on the distal end portion 11 so that the endoscope 3 becomes an endoscope for side view. However, the side illumination optical system including the above-described light transmission optical member may be provided in the distal end portion 11, for example, so that the endoscope 3 itself becomes an endoscope for side view.
(Modification 5)

Furthermore, although the endoscope 3 on which the optical adapter 10 is mounted observes a side portion perpendicular to the axis O in the above-described embodiments and other modifications, the above-described embodiments may be applied to an oblique-viewing optical adapter or endoscope configured to observe a direction in which an emission direction of an illumination optical system is inclined by a predetermined angle to a direction perpendicular to an axis O. In the case, an observation window is arranged to capture light in an oblique direction of a distal end portion of an insertion section, and an illumination window is arranged to emit illumination light in the oblique direction of the distal end portion.

As described above, according to the above-described embodiments and modifications, there can be provided an illumination optical system, an endoscope optical system, and an endoscope in which an amount of leakage of illumination light which leaks out without being totally reflected is reduced to improve transmission efficiency of the illumination light.

Particularly, most of incident light is totally reflected within a light transmission optical member. Accordingly, even when a cross-sectional shape of a light guide is made flat to increase an amount of light, transmission efficiency of illumination light is high. Therefore, much illumination light can be applied to a subject.

Note that, although an example in which an illumination optical system is applied to an endoscope has been described in the above-described embodiments and modifications, the present invention is also applicable to an illumination optical system in another equipment such as an illumination apparatus for color sensor configured to measure a color of an object.

The present invention is not limited to the above-described embodiments, and various changes, alterations, and the like may be made without departing from the scope and spirit of the present invention.

What is claimed is:

1. An illumination optical system comprising:
at least one illumination window provided in a distal end portion of an insertion section configured to be inserted into a subject, the illumination window being configured to emit illumination light in a sideward direction or an oblique direction of the distal end portion; and
an optical member formed into a substantially U shape or a partial shape of the substantially U shape as a cross-sectional shape viewed from a distal end side of a longitudinal axis of the insertion section, the optical member comprising:
an incidence surface on which light directed toward the distal end side from a proximal end side along the longitudinal axis is incident,
an emission surface from which the light is emitted as the illumination light toward the subject, and
at least one reflection surface which is inclined to direct the light incident on the incidence surface toward the emission surface when viewed from the distal end side of the longitudinal axis, wherein the at least one reflection surface is a helical surface formed on the distal end side of the optical member.

2. The illumination optical system according to claim 1, wherein the helical surface is a surface obtained by cutting an outer peripheral surface of the optical member having the substantially U shape along a line segment extending in a direction perpendicular to a central axis of a circular arc of the outer peripheral surface at a predetermined angle to the central axis.

3. The illumination optical system according to claim 2, wherein the reflection surface has a curved surface shape in which a distance z along the central axis is represented by $z=r \times \theta \times A$, where r is a radius of the circular arc, and $\theta$ is an angle in radians from a predetermined position around the central axis, and A is a coefficient.

4. The illumination optical system according to claim 1, wherein the substantially U shape is formed by respective circular arcs of two concentric circles.

5. The illumination optical system according to claim 1, wherein the substantially U shape is formed by two respective circular arcs, which differ in center position, of two circles.

6. The illumination optical system according to claim 1, wherein a shape of the reflection surface is a rectangle when viewed in a direction of the longitudinal axis.

7. The illumination optical system according to claim 1, wherein the at least one reflection surface includes two reflection surfaces provided plane-symmetrically with respect to a plane which passes through a central axis of the distal end portion.

8. The illumination optical system according to claim 7, wherein the at least one illumination window includes two illumination windows.

9. The illumination optical system according to claim 1, wherein the reflection surface is a plane formed on the distal end side of the optical member having the substantially U shape.

10. The illumination optical system according to claim 9, wherein the at least one reflection surface includes two reflection surfaces provided plane-symmetrically with respect to a plane which passes through a central axis of the distal end portion.

11. The illumination optical system according to claim 10, wherein the at least one illumination window includes two illumination windows.

12. An endoscope optical system provided in a distal end portion of an insertion section configured to be inserted into a subject, the endoscope optical system being configured to illuminate and observe a sideward direction or an oblique direction of the distal end portion, the endoscope optical system comprising:
an observation optical system provided in the distal end portion of the insertion section and configured to observe light captured from an observation window configured to capture light in the sideward direction or the oblique direction of the distal end portion; and
an illumination optical system arranged in the distal end portion and including an optical member formed into a substantially U shape or a partial shape of the substantially U shape as a cross-sectional shape viewed from a distal end side of a longitudinal axis of the insertion section such that the observation optical system is arranged inside, the optical member comprising:
an incidence surface on which light directed toward the distal end side from a proximal end side along the longitudinal axis is incident,
an emission surface from which the light is emitted as the illumination light toward the subject, and
a reflection surface which is inclined to direct the light incident on the incidence surface toward the emission surface when viewed from the distal end side of the longitudinal axis, wherein the reflection surface is a helical surface formed on the distal end side of the optical member.

13. The endoscope optical system according to claim 12, wherein the observation optical system emits the light captured from the observation window toward the proximal end side from the distal end side along a longitudinal axis of the insertion section.

14. An endoscope comprising:
an insertion section configured to be inserted into a subject;

an observation window provided in a distal end portion of the insertion section and configured to capture light in a sideward direction or an oblique direction of the distal end portion;

an illumination window provided in the distal end portion of the insertion section and configured to emit illumination light in the sideward direction or the oblique direction of the distal end portion;

an observation optical system provided in the distal end portion of the insertion section and configured to observe the light captured from the observation window; and an illumination optical system arranged in the distal end portion and including an optical member formed into a substantially U shape or a partial shape of the substantially U shape as a cross-sectional shape viewed from a distal end side of a longitudinal axis of the insertion section such that the observation optical system is arranged inside, the optical member comprising:
  an incidence surface on which light directed toward the distal end side from a proximal end side along the longitudinal axis is incident,
  an emission surface from which the light is emitted as the illumination light toward the subject, and
  a reflection surface which is inclined to direct the light incident on the incidence surface toward the emission surface when viewed from the distal end side of the longitudinal axis, wherein the reflection surface is a helical surface formed on the distal end side of the optical member.

15. The endoscope according to claim 14, wherein the observation optical system emits the light captured from the observation window toward the proximal end side from the distal end side along the longitudinal axis of the insertion section.

16. The illumination optical system according to claim 3, wherein θ is within a range from 35° to 55°.

17. The illumination optical system according to claim 1, wherein the light reflected by the reflection surface which is the helical surface is reflected by a side surface of the optical member and emitted.

18. An optical adapter configured to removably connect to a distal end portion of an insertion section of an endoscope, the optical adapter comprising:
  an illumination optical system comprising:
    at least one illumination window configured to emit illumination light in a sideward direction or an oblique direction of the distal end portion; and
    an optical member formed into a substantially U shape or a partial shape of the substantially U shape as a cross-sectional shape viewed from a distal end side of a longitudinal axis of the insertion section, the optical member comprising:
      an incidence surface on which light directed from the distal end portion along the longitudinal axis is incident,
      an emission surface from which the light is emitted as the illumination light toward the subject, and
      at least one reflection surface which is inclined to direct the light incident on the incidence surface toward the emission surface when viewed from the distal end side of the longitudinal axis, wherein the at least one reflection surface is a helical surface formed on the distal end side of the optical member.

* * * * *